United States Patent
Murayama et al.

(10) Patent No.: US 6,282,458 B1
(45) Date of Patent: Aug. 28, 2001

(54) METHODS AND SYSTEMS FOR CONTROLLING OLFACTORY STIMULI

(75) Inventors: Noboru Murayama, Tokyo; Satoshi Yamauchi; Koichi Suzuki, both of Kanagawa, all of (JP)

(73) Assignee: Ricoh Company, Ltd. (JP)

( * ) Notice: Subject to any disclaimer, the term of this patent is extended or adjusted under 35 U.S.C. 154(b) by 0 days.

(21) Appl. No.: 09/364,422

(22) Filed: Jul. 30, 1999

Related U.S. Application Data

(63) Continuation-in-part of application No. 08/932,146, filed on Sep. 17, 1997.

(30) Foreign Application Priority Data

Sep. 17, 1996 (JP) .................................................. 8-245292
Jul. 18, 1997 (JP) .................................................. 9-194291

(51) Int. Cl.[7] .................................................. G06F 17/00
(52) U.S. Cl. ..................... 700/239; 700/241; 700/265; 422/5; 422/108
(58) Field of Search .................................. 700/239, 241, 700/265; 222/3; 73/23.34, 23.36; 422/5, 123, 108

(56) References Cited

U.S. PATENT DOCUMENTS

| | | | |
|---|---|---|---|
| 2,813,452 | 11/1957 | Laube | 422/4 |
| 2,905,049 | 9/1959 | Laube | 422/4 |
| 3,050,870 | 8/1962 | Heilig . | |
| 3,661,323 | 5/1972 | Farris | 422/114 |
| 3,795,438 | 3/1974 | Westenholz et al. | 422/5 |
| 4,102,656 | 7/1978 | Koritz . | |
| 4,402,856 | 9/1983 | Schnoring et al. . | |
| 4,444,720 | 4/1984 | Mayer | 422/4 |
| 4,556,539 | 12/1985 | Spector | 422/4 |
| 4,629,604 | 12/1986 | Spector | 422/5 |
| 4,952,400 | 8/1990 | Tararuj et al. | 428/905 |
| 5,018,974 | 5/1991 | Carnahan et al. | 428/905 |
| 5,023,020 | 6/1991 | Machida et al. | 422/124 |
| 5,071,621 | 12/1991 | Tokuhiro et al. | 422/4 |
| 5,105,133 | 4/1992 | Yang | 422/124 |
| 5,178,839 | 1/1993 | Spector | 422/4 |
| 5,356,458 | 10/1994 | Javadi et al. . | |
| 5,398,070 | 3/1995 | Lee . | |
| 5,591,409 | 1/1997 | Watkins | 422/5 |
| 5,648,046 | 7/1997 | Weibel | 422/4 |
| 5,724,256 | 3/1998 | Lee et al. | 422/5 |
| 5,788,569 | 8/1998 | Lee | 454/229 |

FOREIGN PATENT DOCUMENTS

| | | |
|---|---|---|
| 4018020 | 12/1990 | (DE) . |
| 4135796 | 6/1993 | (DE) . |
| 0398687 | 11/1990 | (EP) . |
| 0616175 | 9/1994 | (EP) . |
| 5-146499 | 6/1993 | (JP) . |
| 8-336576 | 12/1996 | (JP) . |
| WO 94/09493 | 4/1994 | (WO) . |

OTHER PUBLICATIONS

"Web Adds Postcards Bulb Jokes", Arizona Republic/Phoenix Gazette (AZ), Aug. 19, 1996, by David Hoye.*
Japanese Abstract: Application No. 03314317, filed Nov. 28, 1991 entitled "Perfuming Device".
Japanese Abstract: Application No. 01237998, filed Sep. 13, 1989 entitled "Fragrance Feeding Apparatus".
Japanese Abstract: Appliction No. 06292287, filed Mar. 31, 1993 entitled "Body Feeling Device".

* cited by examiner

Primary Examiner—Christopher P. Ellis
Assistant Examiner—Khoi M. Tran
(74) Attorney, Agent, or Firm—Knoble & Yoshida, LLC

(57) ABSTRACT

The system and method of controlling the olfactory stimuli release a specified aroma-causing agent from a first specified location in environment. In order to simulate the movement of the released aroma-causing agent in space, the same aroma-causing agent is released from a second specified location in the environment.

18 Claims, 21 Drawing Sheets

FIG. 16A

| HUMIDITY | TEMPERATURE | RELEASE DURATION | RELEASING UNIT | SCENT | NUMBER |
|---|---|---|---|---|---|
| 70% ~ OVER | ~18°C | 10 | B5 | BANANA | ① |
| | 18°C~25°C | 30 | A1 | PINE | ② |
| | 25°C~ | 20 | B1 | MINT | ③ |
| 30% ~ 70% | ~18°C | 10 | B6 | MANGO | ④ |
| | 18°C~25°C | 30 | A3 | OAK | ⑤ |
| | 25°C~ | 60 | — | NEGATIVE ION | ⑥ |
| UNDER ~ 30% | ~18°C | 10 | B7 | PAPAYA | ⑦ |
| | 18°C~25°C | 40 | A5 | BEECH TREE | ⑧ |
| | 25°C~ | 15 | B2 | JASMINE | ⑨ |

FIG. 16C

| SQ | A STEP PROCESS | RELEASING UNIT # | RELEASING TIME | INTERNAL | RELEASING TIME |
|---|---|---|---|---|---|
| 1 | Negative Ion | – | 180 sec. | – | 180 sec. |
| 2 | A mugwort release | A6 | 120 sec. | 50 sec. | 20 sec. |
| 3 | A mugwort removal | B6 | 30 sec. | – | 30 sec. |
| 4 | An iris release | A8 | 270 sec. | 60 sec. | 15 sec. |
| 5 | An iris removal | B8 | 30 sec. | – | 30 sec. |
| 6 | A convolvulus release | B10 | 270 sec. | 60 sec. | 30 sec. |
| 7 | Negative Ion | – | 180 sec. | – | 180 sec. |
| 8 | A perilla release | A12 | 180 sec. | 50 sec. | 20 sec. |
| 9 | A perilla removal | B12 | 30 sec. | – | 30 sec. |
| 10 | Wild chrysanthemum | A15 | 530 sec. | 90 sec. | 30 sec. |
| 11 | EOF | – | – | – | – |

METHODS AND SYSTEMS FOR CONTROLLING OLFACTORY STIMULI

CROSS-REFERENCES TO RELATED APPLICATIONS

This application is a continuation-in-part of application Ser. No. 08/932,146, filed Sep. 17, 1997, which was a U.S. filing of Japanese Application Nos. 8-245292 dated Sep. 17, 1996 and 9-194291 dated Jul. 18, 1997.

FIELD OF THE INVENTION

The current invention is generally related to methods and systems for controlling olfactory stimuli, and more particularly related to the methods and the system for controlling the olfactory stimuli to provide directionality based upon an input signal.

BACKGROUND OF THE INVENTION

Olfactory stimuli often elicit certain responses in humans. For example, certain olfactory stimuli generally make us feel refreshed while others make us feel nauseated. Yet other olfactory stimuli increase our appetite. In other words, olfactory stimuli have a wide variety of roles and effects in our daily lives. Such a variety of effects is reflected in languages such as in Japanese in which three different characters respectively express "aroma," "desirable scent" and "undesirable odor." However, despite the wide variety of scents that humans perceive, according to one theory, there are only 20 to 30 original scents, and the wide variety is generated by the combinations of these original scents.

To control the variety of undesirable odor, various products have been available. For example, deodorants and perfumes overpower body odors while air refreshers control undesirable odors. These products generally suppresses an existing odor by an overwhelming additional odor. In contrast to the above described suppression, certain other products such as bathroom products neutralize an existing undesirable odor. For example, a certain solid product is sublimated for reacting with an odor-causing agent such as ammonia in the air so as to neutralize it.

In contrast, desirable scents are used for elevating mood or promoting ambience. In fact, the use of certain aroma-causing agents has been known in aroma therapy for relaxation of body and mind. Olfactory stimuli are generated by incense burning or releasing aroma-causing agents in the air. In this regard, "Scent and Environment" Iwasaki, (Science and Engineering Books Kabushiki Kaisha, Feb. 25, 1997) discloses an aroma dispensing system which is incorporated into an air conditioning system. The aroma dispensing system circulates a selected aroma-causing agent through air ducts based upon a control signal. However, the control signal is limited to the relatively constant generation of a selected scent.

The above described scent generation system is generally limited in its capability to quickly adapt to a new circumstance. In other words, the above system is substantially static and lacks dynamic adaptation over a short period of time. Thus, it is desired that a scent generation system is able to respond to control signals each of which specifies one of a variety of distinctive olfactory stimuli. A selected scent should be presented without being affected by an existing or residual scent in the environment. Furthermore, it is also desired that the control signals are generated in response to certain conditions of the environment.

SUMMARY OF THE INVENTION

In order to accomplish the above and other objectives, according to one aspect of the current invention, a method of controlling olfactory stimuli, including the steps of: a) releasing a first aroma-causing agent in environment; b) storing information on the first aroma-causing agent; c) releasing a first aroma-removing agent in the environment based upon the information stored in the step b); and d) releasing a second aroma-causing agent in the environment after the step c).

According to a second aspect of the current invention, a method of controlling olfactory stimuli, including the steps of: a) measuring a predetermined characteristic of environment; b) generating an environmental signal; and c) releasing a first aroma-causing agent in the environment based upon the environmental signal.

According to a third aspect of the current invention, a system for controlling olfactory stimuli, including: an environmental measuring unit for measuring a predetermined characteristic of environment and generating an environmental signal; a controller connected to the environmental measuring unit for generating an aroma releasing signal in response to the environmental signal; an aroma storage unit for storing a plurality of aroma-causing agents; and an aroma releasing unit connected to the controller and the aroma storage unit for selectively releasing one or more of the aroma-causing agents in the environment based upon the environmental signal.

According to a fourth aspect of the current invention, a system for controlling olfactory stimuli, including: an environmental measuring unit for measuring a predetermined characteristic of environment and generating an environmental signal; a controller connected to the environmental measuring unit for generating an aroma releasing signal in response to the environmental signal; an aroma storage unit for storing a plurality of aroma-causing agents; and an aroma releasing unit connected to the controller and the aroma storage unit for selectively releasing one or more of the aroma-causing agents in the environment based upon the environmental signal.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 16A is an exemplary table of information on a selection of scents and a set of selection criteria which is used in the olfactory stimuli control system according to the current invention.

FIG. 16C is another exemplary table of information on a sequential selection of scents used in the olfactory stimuli control system according to the current invention.

DETAILED DESCRIPTION OF THE PREFERRED EMBODIMENT(S)

Figure 1:
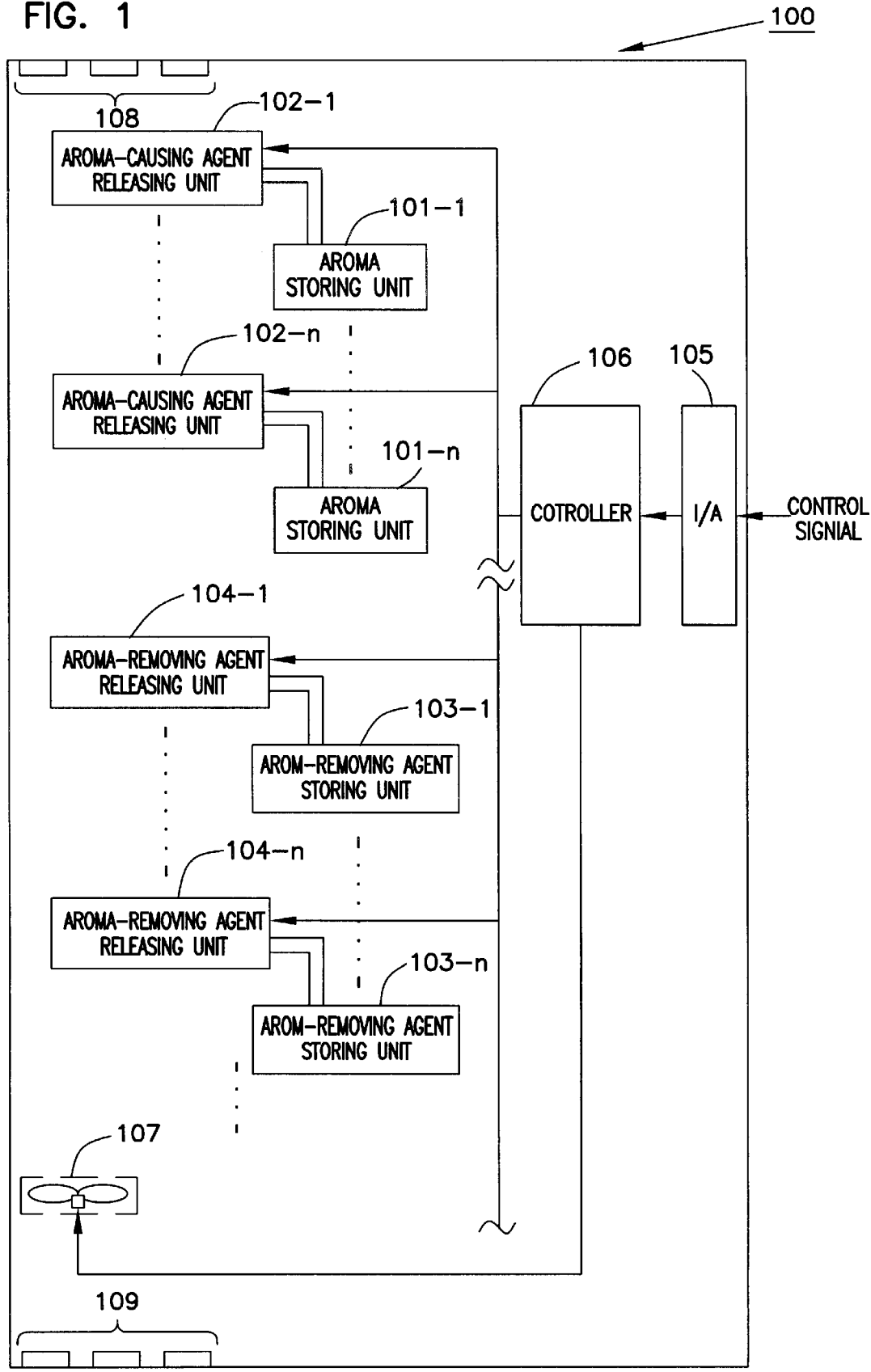
FIG. 1 diagrammatically illustrates one preferred embodiment of the olfactory stimuli control system according to the current invention.

Referring now to the drawings, wherein like reference numerals designate corresponding structure throughout the views, and referring in particular to FIG. 1, one preferred embodiment of the system for controlling olfactory stimuli is graphically illustrated. The olfactory control system 100 receives an input control signal through an interface unit (I/F) 105, and a controller 106 selectively activates one or more of aroma-causing agent releasing units or aroma releasing units 102-1 through 102-n based upon the input control signal (102-2 through 102-(n-1) are not individually illustrated). Each of the releasing units 102-1 through 102-n is connected to a corresponding independent aroma storing unit 101-1 through 101-n (101-2 through 101-(n-1) are not individually illustrated), and each aroma storing unit contains an aroma-causing agent. Thus, n distinctive aroma-causing agents stored in n aroma-storing units can make up to $2^n-1$ combinations of scents. Similarly, the controller 106 also selectively activates one or more of aroma-removing agent releasing units 104-1 through 104-n based upon the input control signal (104-2 through 104-(n-1) are not individually illustrated). Each of the aroma-removing agent releasing units 104-1 through 104-n is connected to a corresponding independent aroma-removing agent storing unit 103-1 through 103-n (103-2 through 103-(n-1) are not individually illustrated), and each aroma-removing agent storing unit contains an aroma-removing agent. A fan 107 is selectively activated based upon the input control signal for causing an air flow containing the above released agents from an air input vent 109 towards an air output vent 108.

Still referring to FIG. 1, as described above, the input control signal specifies the activation of one or more of the aroma-causing agent releasing units 102-1 through 102-n and or one or more of the aroma-removing agent releasing units 104-1 through 104-n. As a result of simultaneous activation of certain selected aroma-causing agent releasing units 102-1 through 102-n, a plurality of the released aroma-causing agents is mixed prior to outputting through the air output vent 108. In such a mixture, the mixture is referred to as a single aroma-causing agent while the mixed aroma-causing agents are referred to as elements. Such a mixture of the aroma-causing agents generates a scent that may be distinct from any one of the stored aroma-causing agents in the system. Information on the released aroma-causing agents or the input control signal is stored in the controller 106. In order to control existing aroma which has been already released by the system prior to outputting a new scent, the input control signal or the stored information is retrieved for activating one or more of the aroma-removing agent releasing units so as to release appropriate aroma-removing agents which deactivate, suppress or remove the existing scent.

Figure 2:
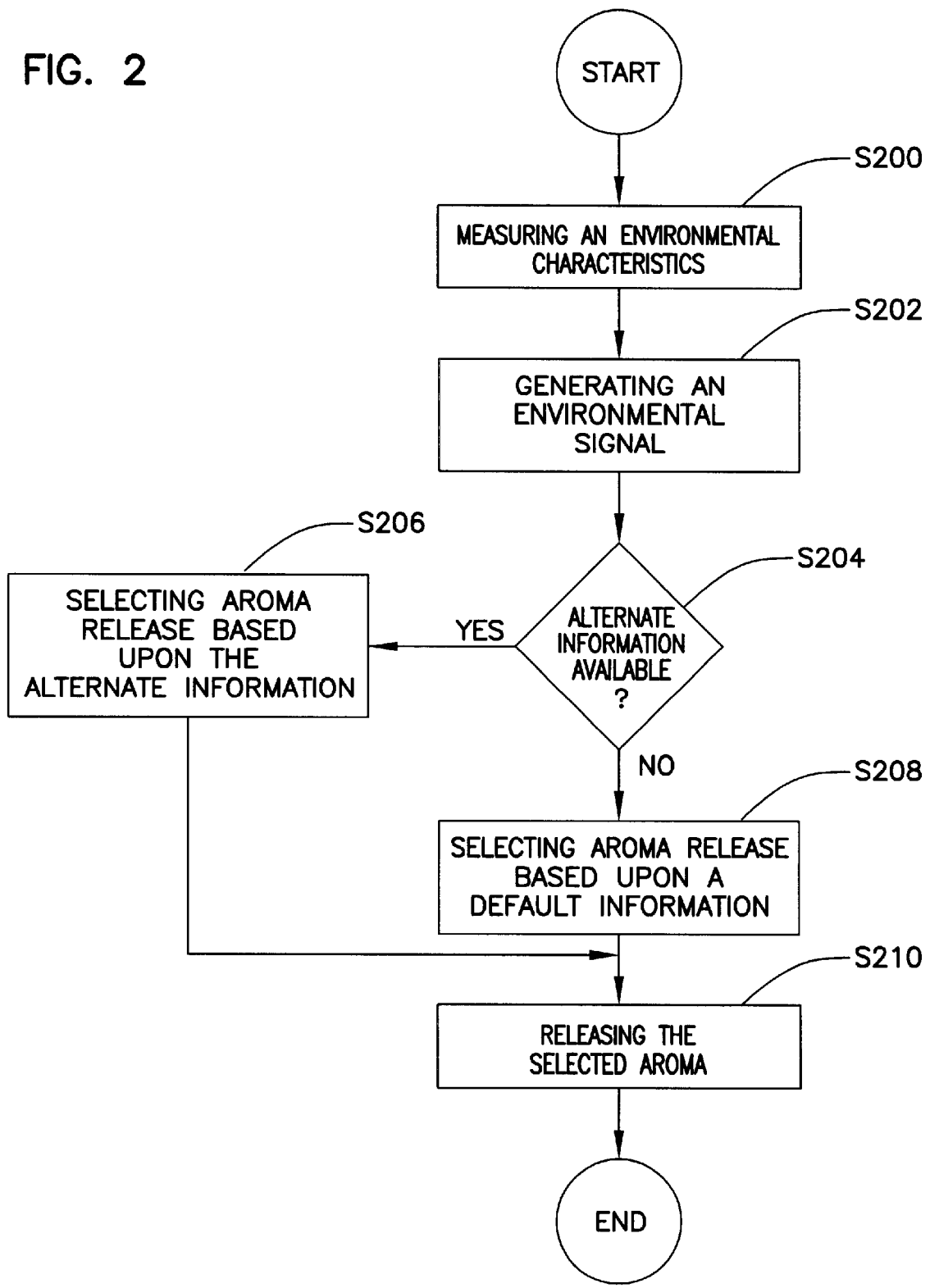
FIG. 2 is a flow chart illustrating steps involved in one preferred process of generating olfactory stimuli according to the current invention.

Now referring to FIG. 2, a flow chart illustrates some of the steps involved in a preferred process of controlling olfactory stimuli. Based upon an input signal, a single aroma or a combination of scents is released in a step S150. The input signal itself or information on the released aroma is stored in a step S152 for the future use. The information includes not only the type of each released aroma-causing agent, but also the released quantity such as duration or concentration of the aroma-causing agent. In a Step 154, based upon the above stored information, a corresponding aroma-removing agent or a corresponding combination of aroma-removing agents is released so that the release aroma no longer affects the environment. The aroma-removing agent may suppresses, neutralizes or overpowers the existing aroma so as to invalidate the effect of an existing aroma. At this point, a new aroma-causing agent may be released in the same environment based upon a new or the same input signal so as to repeat the above described process. On the other hand, the process ends in a step S156.

Figure 3A:
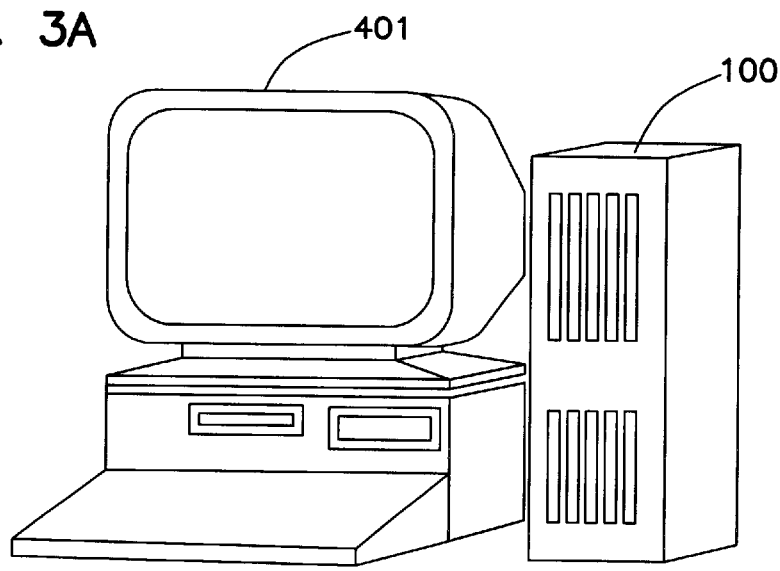
FIGS. 3A and 3B respectively illustrate some exemplary combinations of the olfactory control system and computer systems according to the current invention.

Now referring to FIG. 3A, one preferred embodiment 100 of the olfactory stimuli system according to the current invention is connected to a personal computer (PC) 401, which provides an input control signal to the olfactory stimuli system 100. At the same time, the personal computer

Figure 3B:
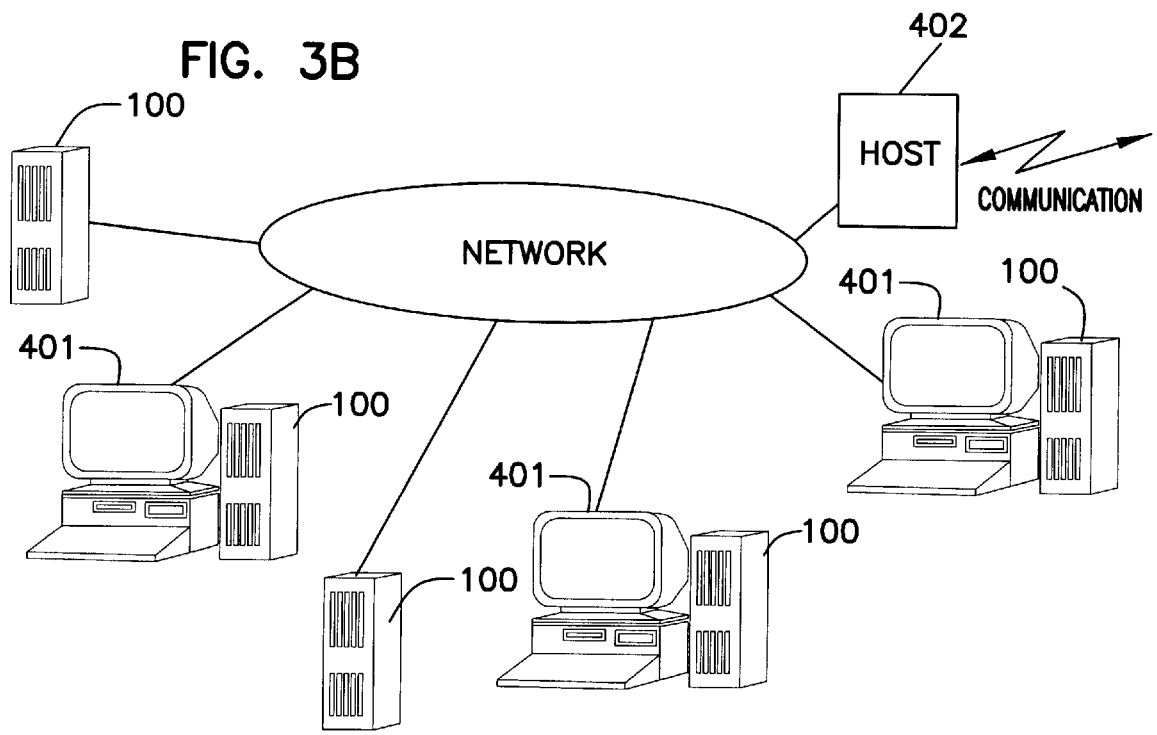

401 provides a set of audio-visual stimuli to complement the olfactory stimuli. The above PC-combined olfactory system 100, 401 is further combined with other similarly combined systems 100, 401 as well as the systems alone 100 via a network link such as LAN and Internet as shown in FIG. 3B. In addition, a host computer 402 is optionally connected to the network and provides an input signal or information for specifying an aroma to be generated by the olfactory system 100.

Still referring to FIGS. 3A and 3B, the above described network olfactory stimuli systems are used to generate virtual experiences. For example, using Internet, a host computer 402 simulates a web site for a mini-mall consisting of a produce store, a florist, a bakery and etc. Upon visiting the virtual produce store, both visual and olfactory data is downloaded to a local PC so that not only visual images for example of bananas and pineapples are displayed at a PC monitor, but also their respective scent is also generated by the olfactory system 100. The scent complements the visual audio stimuli to improve the virtual experiences. Another example of the use of the olfactory system in the network includes the aroma gram in e-mail. In addition to sending textual information, an aroma signal or standard coded scent data is attached to the e-mail so that the data is decoded to generate an intended aroma upon opening the e-mail. Of course, to accomplish the above described use of aroma in an network environment, a sending side and a receiving side must share the same scent coding data, and the receiving side must be equipped with an olfactory stimuli system with storage units containing the specified aroma-causing agents.

In another use of the above-described network of the olfactory stimuli systems one of the local PC units 401 is selected based upon the input signal from the host unit 402, and the input signal includes information on a first releasing location and an aroma-causing agent. Each PC unit 401 is placed at a specific predetermined location in network environment and is assigned a unique specific location ID. A control unit in each of the PC units 401 decodes the input signal to determine whether or not a specified aroma-causing agent is to be released from the unit which is the closest to a specified location. Furthermore, the input signal includes information on an additional second releasing location and a time delay following the first release. A combination of the first release and the second release simulates a movement of the aroma-causing agent in space or provides directionality of the aroma in the environment.

Figure 4:
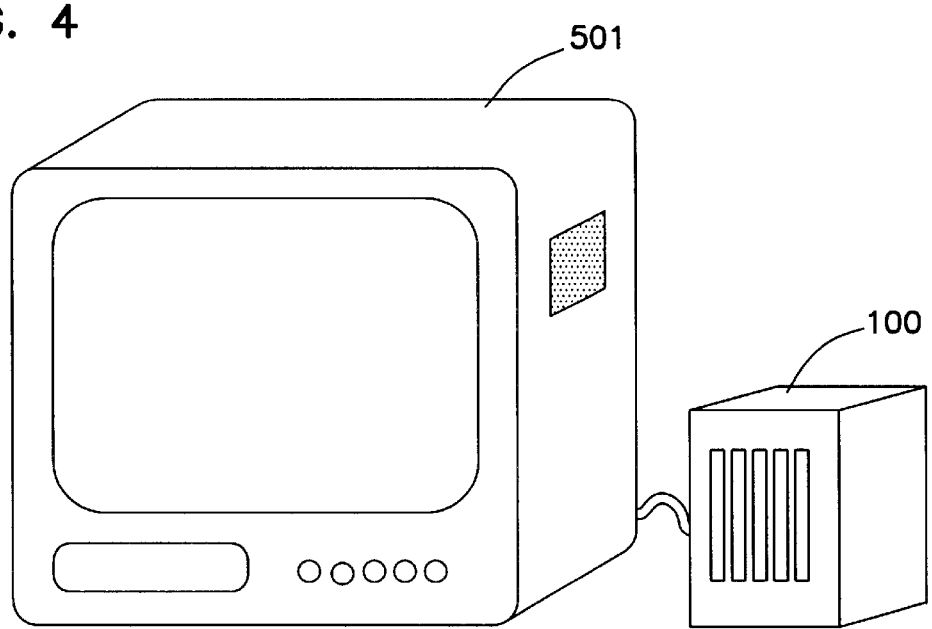
FIG. 4 illustrates another exemplary combination of the olfactory control system and a television set according to the current invention.

Now referring to FIG. 4, one preferred embodiment 100 of the olfactory stimuli system according to the current invention is connected to a television set (TV) 501, which provides audiovisual stimuli and an input control signal to the olfactory stimuli system 100. The input control signal is included in a TV broadcast signal, and upon receiving the TV signal, the TV set 501 generates audio-visual stimuli while outputting the input control signal to the olfactory system 100. The olfactory system 100 generates an olfactory stimulus based upon the input control signal to complement the audio-visual stimuli provided by the TV set 501. In general, contrast to a large amount of data for audio-visual information, since accompanying olfactory information is relatively limited, the olfactory signal is easily waved in the audio-visual signals. The use of the above described olfactory-stimuli includes enhanced TV experiences in simulating background aroma or odor. For example, for the audio-visual stimuli background scene in the forest is enhanced by generating aromas related to trees while an oceanic background becomes more realistic by generating salt water odor.

Figure 5:
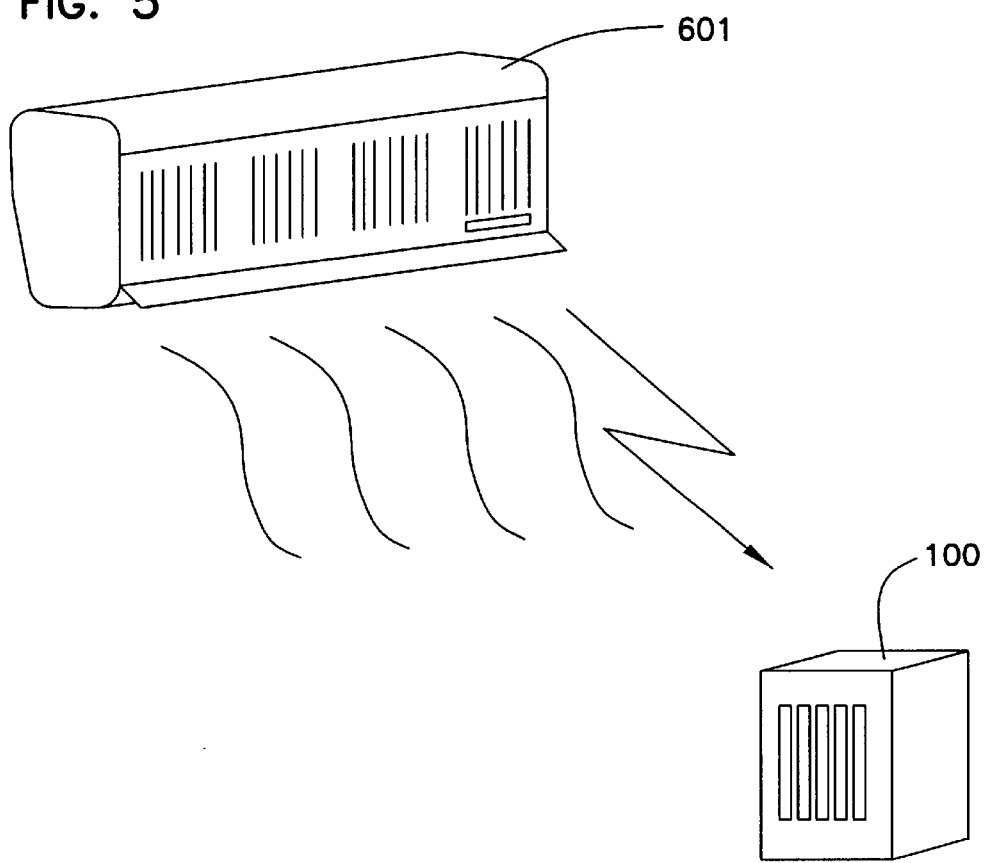
FIG. 5 illustrates another exemplary combination of the olfactory control system and an air conditioner according to the current invention.

Now referring to FIG. 5, one preferred embodiment 100 of the olfactory stimuli system according to the current invention is connected to an air conditioner (AC) 601, which provides an input control signal to the olfactory stimuli system 100. To determine what scent is to be generated by the olfactory system 100, for example, based upon a temperature that the AC 601 is set, the AC 601 generates an input control signal which is transmitted to the olfactory system 100 via infrared. In particular, during a cold season, a tropical scent such as tropical fruit aroma including mango, papaya and pineapple may be dispensed to counterbalance the temperature while during a warm season, a certain herb aroma may be dispensed. Another example is that during an air blowing period without altering the temperature, a scent of forest may be dispensed. In contrast to the above preselected scents, a scent may be also selected by a user via a remote control. Lastly, an alternative embodiment of the olfactory stimuli system 100 may be included in an AC unit rather than a separate unit.

Figure 6:
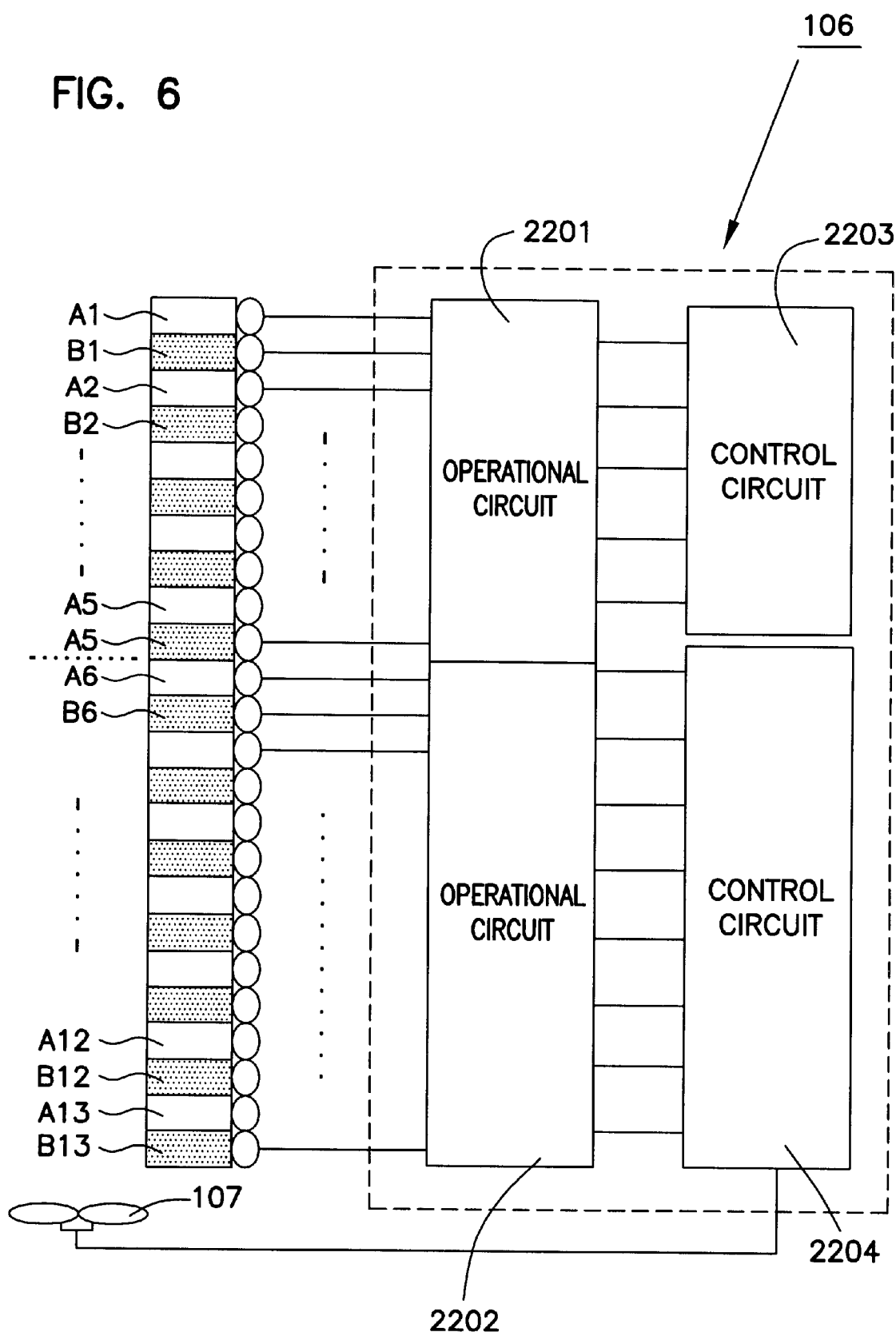
FIG. 6 illustrates a circuit diagram of a controller along with certain other components of the olfactory stimuli control system according to the current invention.

FIG. 6 diagrammatically illustrates certain components of a controller 106 as shown in FIG. 1. One implementation of the controller 106 includes a pair of control circuits 2203 and 2204 as well as a pair of corresponding operational circuits 2201 and 2202. In general, the control circuits 2203 and 2204 select certain operation of the operational circuits 2201 and 2202 for physically activating the selected releasing units. The control circuits 2203 and 2204 also control the operation of a fan 107 for generating an air flow after the selected aroma-causing agents are released. The control circuit 2203 via the operational circuit 2201 ultimately controls a set of aroma-causing agent releasing units A1 through A5 as well as corresponding aroma-removing agent releasing units B1 through B5. Similarly, the control circuit 2204 via the operational circuit 2202 ultimately controls a set of aroma-causing agent releasing units A6 through A13 as well as corresponding aroma-removing agent releasing units B6 through B13. Thus, the control circuits 2203 and 2204 control the generation of a selected scent which may be a mixture of the aroma-causing agents. After the release of the selected scent, the control circuits 2203 and 2204 also control the removal, neutralization or suppression of the released scent by a mixture of the aroma-removing agents.

Figure 7:
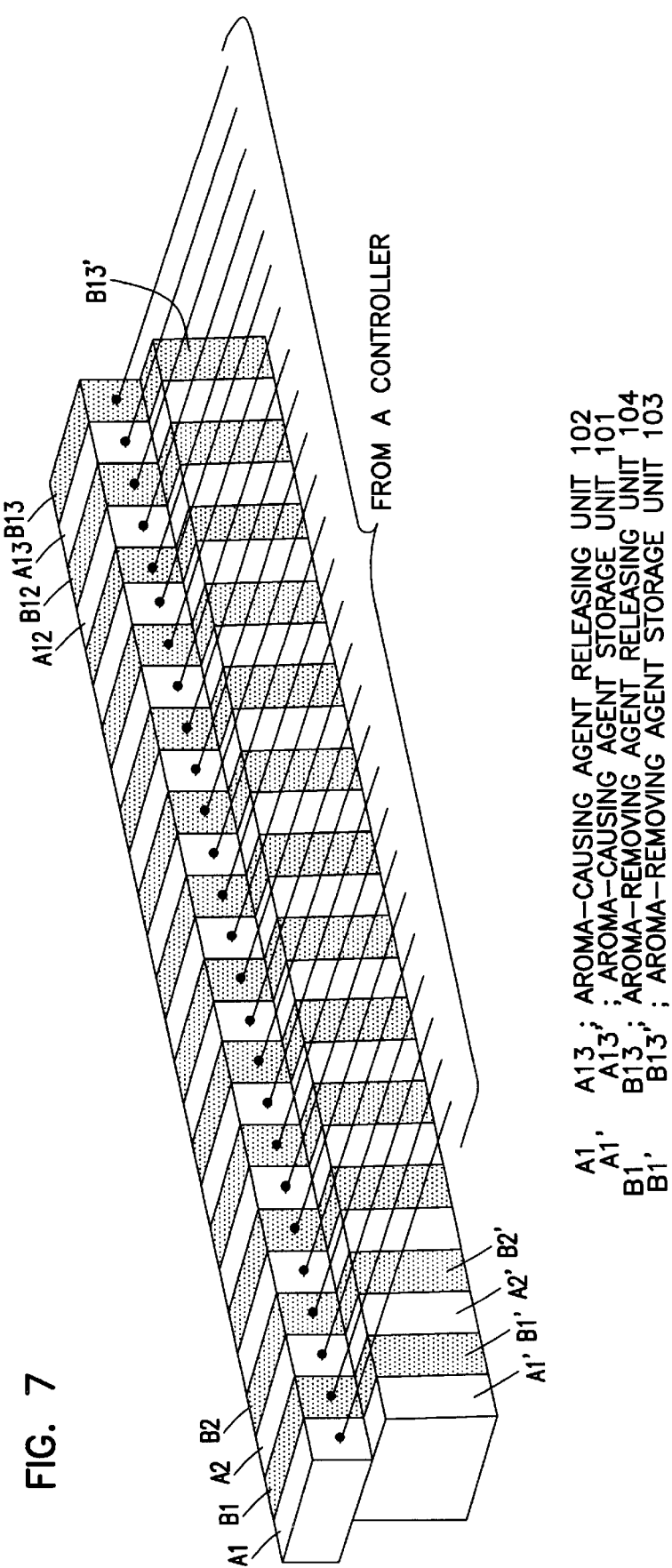
FIG. 7 is a schematic for illustrating an exemplary arrangement of olfactory releasing units used in the olfactory stimuli control system according to the current invention.

Now referring to FIG. 7, a perspective view illustrates one preferred arrangement of the above described aroma-causing agent releasing units A1 through A13 and aroma-removing agent releasing units B1 through B13. Each of these units is independently controlled by a controller. In this arrangement, one aroma-causing agent releasing unit and its corresponding aroma-removing agent releasing unit are alternately juxtaposed. Furthermore, each of the aroma-causing agent releasing units A1 through A13 is placed adjacent to its corresponding one of aroma-causing agent storage unit A1' through A13' while each of the aroma-removing agent releasing units B1 through B13 is also placed adjacent to its corresponding one of aroma-removing agent storage units B1' through B13'. Close proximity of the releasing units A1 through A13 as well as B1 through B13 promotes efficient mixture of the released agents before outputted from the olfactory stimuli system.

Figure 8:
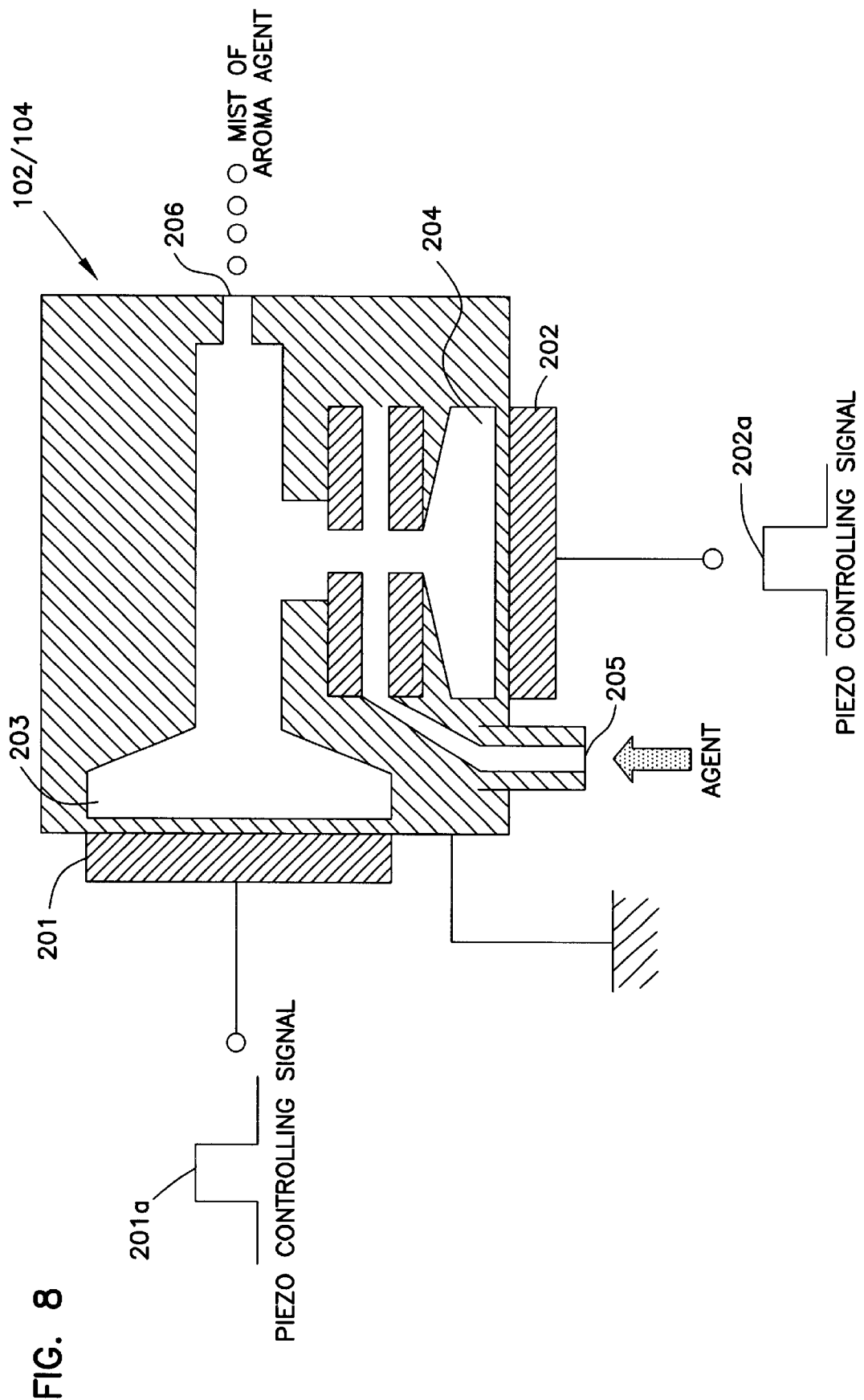
FIG. 8 is a cross sectional view of one preferred embodiment of the releasing unit used in the olfactory stimuli control system according to the current invention.

Referring to FIG. 8, one preferred embodiment of the releasing unit according to the current invention is diagrammatically illustrated in a cross sectional view. In general, the preferred embodiment is substantially similar to an On-demand-type ink-jet printer head with piezoelectric vibrators for discharging an aroma-causing agent or an aroma-removing agent. In general, an aroma-causing agent releasing unit 102 is substantially identical to an aroma-removing agent releasing unit 104 except for the agent to be released. Each releasing unit includes a pair of piezoelectric vibrators 201 and 202 which are located outside of a housing near a corresponding cavity 203 and 204. An agent enters the releasing unit 102 or 104 through an input pipe 205, and the vibration causes the liquid agent to discharge through an output nozzle 206 in mist. The piezoelectric vibrators 201 and 202 are activated by a predetermined frequency signal. An alternative embodiment of the releasing unit includes an on-demand type bubble-jet printer head.

Figure 9:
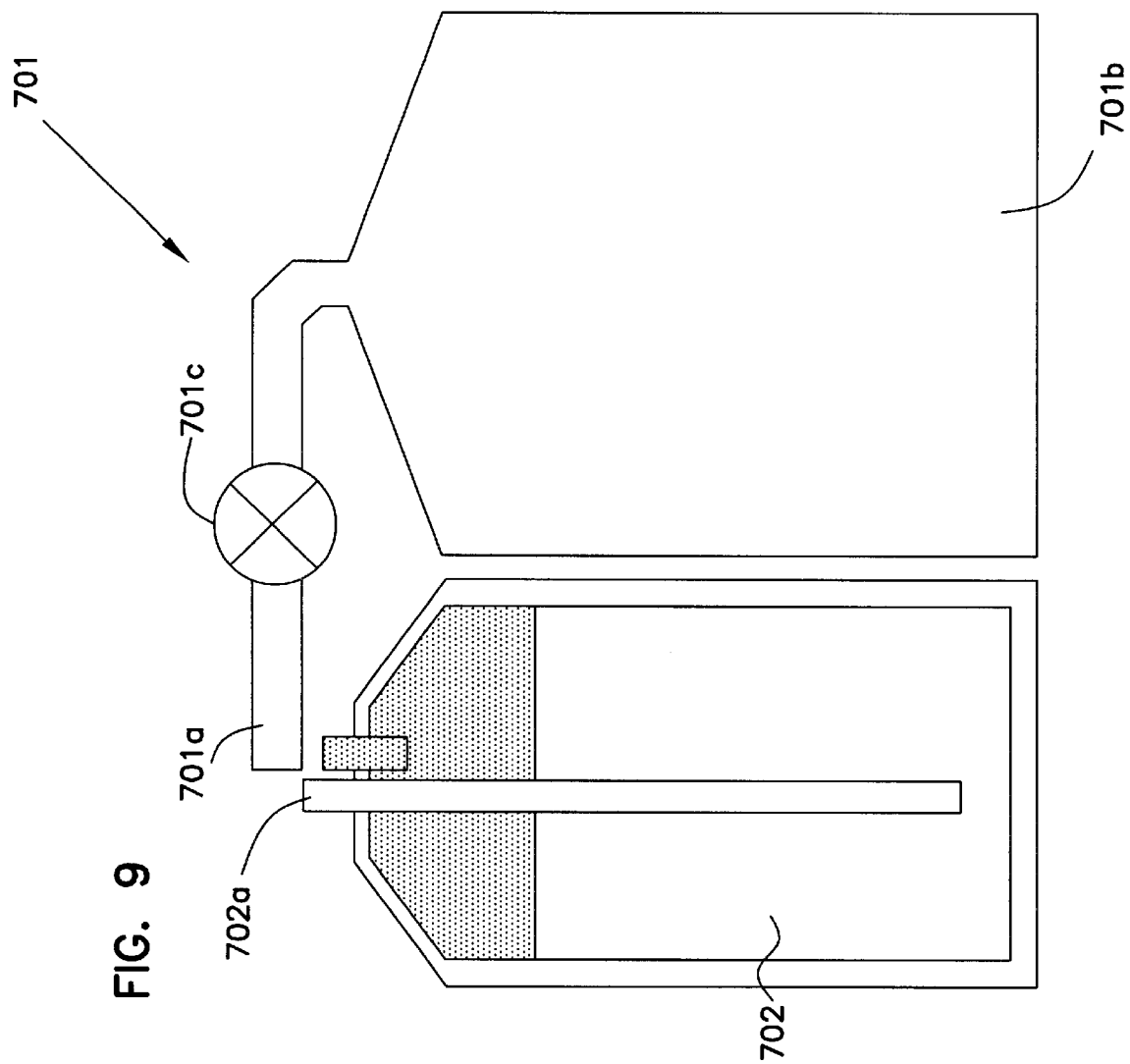
FIG. 9 is a cross sectional view of a second preferred embodiment of the releasing unit used in the olfactory stimuli control system according to the current invention.

Now referring to FIG. 9, a second preferred embodiment of the releasing unit according to the current invention is diagrammatically illustrated in a cross sectional view. A sprayer 701 generates mist or spray of an aroma agent stored in a storage unit 702 near an air nozzle 701 and an aroma liquid releasing nozzle 702a at an onset of an electromagnetic valve 701c for releasing compressed air stored in a compressed air tank 701b. In general, the second preferred embodiment is suitable for releasing a large amount of an aroma-causing agent and or an aroma-removing agent. Alternative embodiments of the second embodiments include air compressor in lieu of the compressed air tank 701b as well as introducing the compressed air in the aroma liquid storage tank for generating spray.

Figure 10:
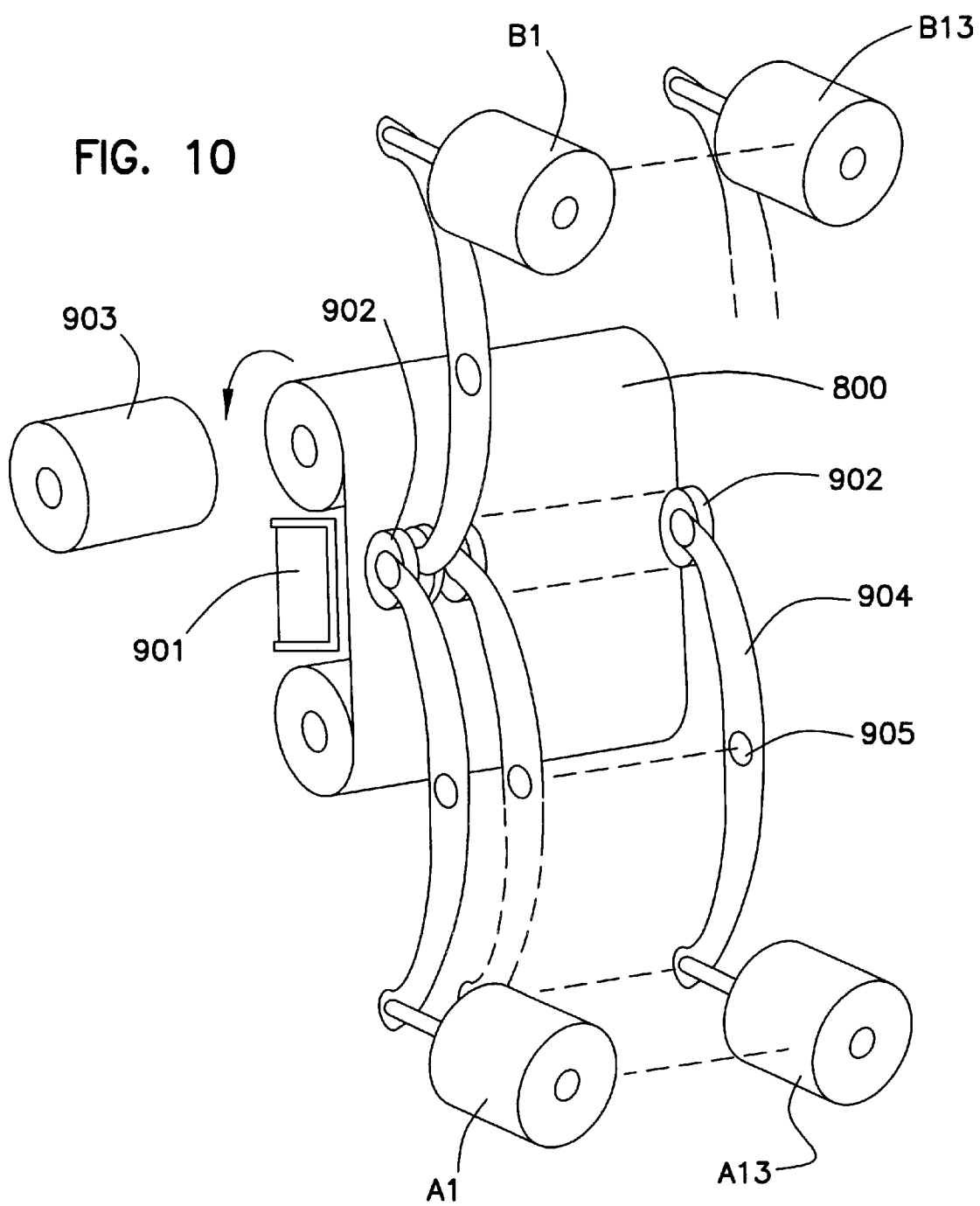
FIG. 10 is a perspective view of a third preferred embodiment of the releasing unit used in the olfactory stimuli control system according to the current invention.

Referring to FIG. 10, a third preferred embodiment of the releasing unit according to the current invention is illustrated in a perspective view. In general, the third preferred embodiment mechanically breaks and or squeezes an aromatic agent stored in a capsule. Each capsule is placed on a roll 800 and placed over a board 901. When a corresponding one of plungers A1 through A13 or B1 through B13 is activated in such a way that a roller 902 is pressed against the roll 800 via a pivot 905, the capsule is broken and consequently the stored aromatic agent is released in the air. A plurality of the plungers is simultaneously activated to cause a selected combination of the agents to be released in the air. Alternatively, the size of the roller 902 is modified to rupture either a single capsule or a plurality of capsules. After the selected activation, the roll 800 is rolled over a retracting roll via a driving motor 903 as indicated by an arrow. As the exposed capsules are retracted, the ruptured portion may be automatically sealed by a piece of tape so that the residual agent is substantially prevented from being continuously released. After retracting the roll 800, a new portion of the unbroken capsule is placed over the board 901 for the next activation. It is also possible to continuously release the agent by moving the roll 800 while pressing the roller 902 against the roll 800.

Figure 11A:
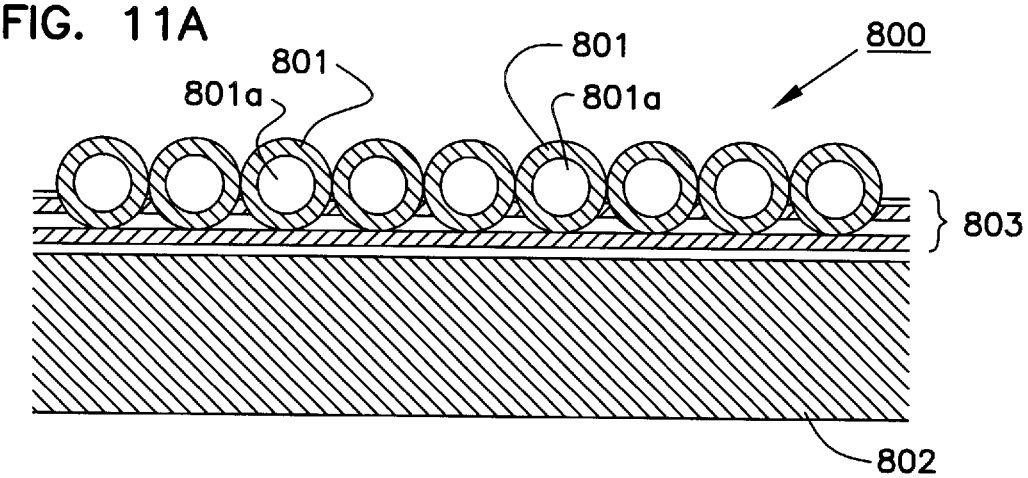
FIGS. 11A and 11B are respectively a cross sectional view and a top view of an aroma storage unit used in the olfactory stimuli control system according to the current invention.
Figure 11B:
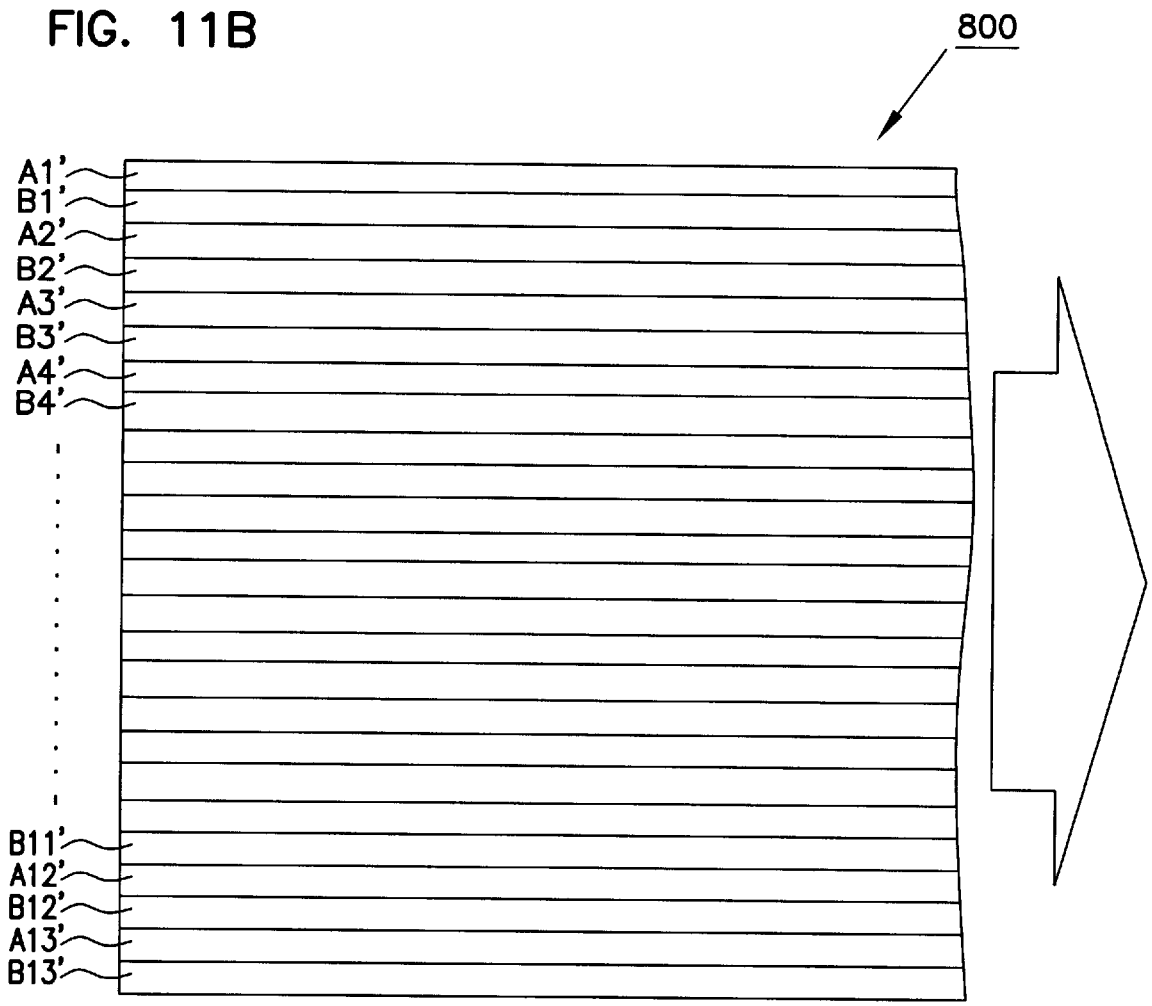

Referring to FIGS. 11A and 11B, some detailed construction of the roll 800 is further described. FIG. 11A illustrates a cross sectional view. The roll 800 includes a predetermined number of capsules 801, each of which contains either an aroma-causing agent or an aroma-removing agent 801a. The capsules 801 containing the agent 801a are fixed on a roll substrate 802 with a binder 803. Some examples of the roll substrate include a sheet of paper, cloth and plastic. As described above, the capsules 801 is each ruptured in response to a predetermined amount of pressure or heat for releasing the content. FIG. 11B illustrates a top view of the roll 800. According to one preferred embodiment, aroma-causing agent containing capsules A1' through A13' and aroma-removing agent containing capsules B1' through B13' are alternately juxtaposed in the direction of moving the roll 800.

Figure 12:
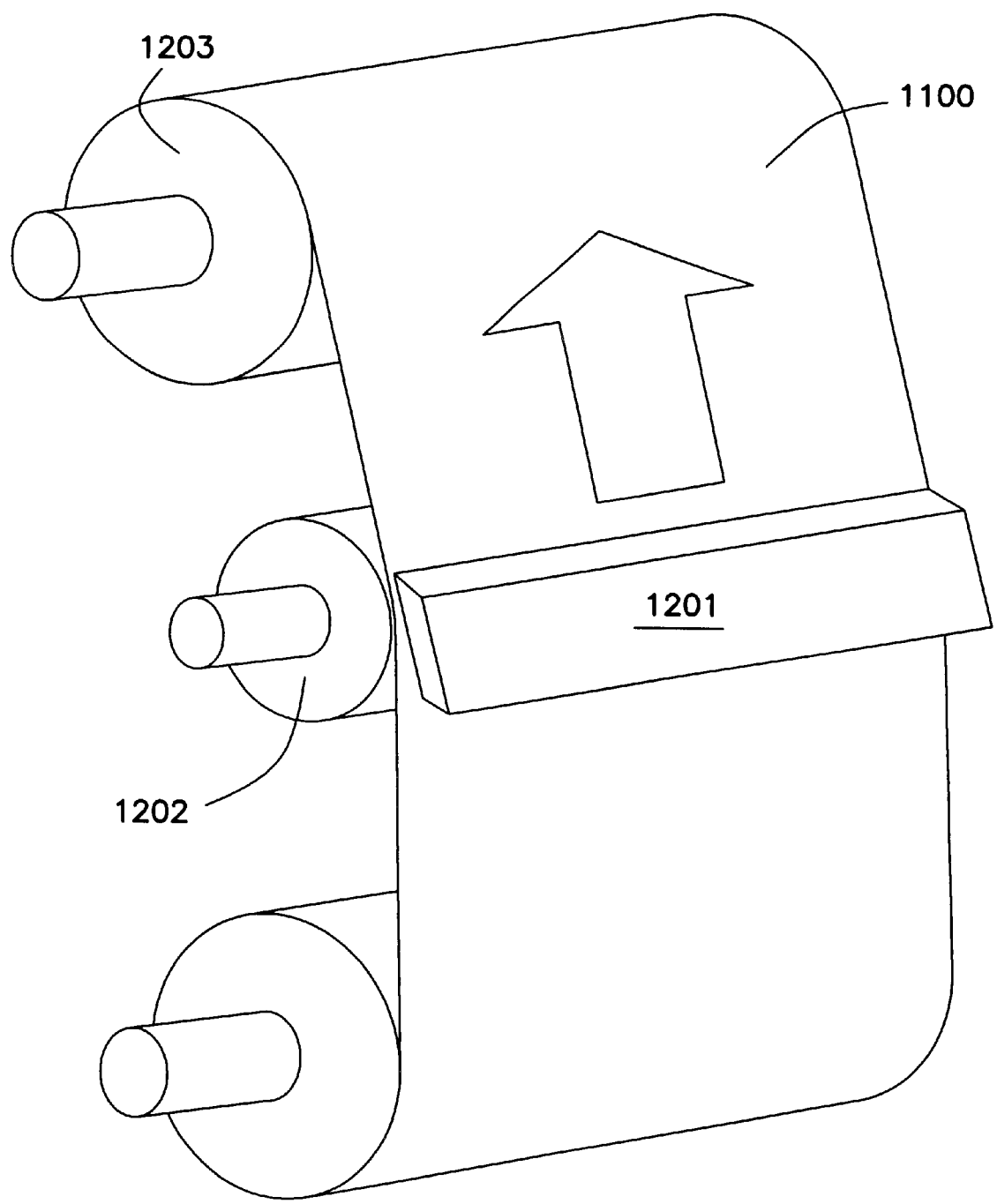
FIG. 12 is a perspective view of a fourth preferred embodiment of the releasing unit used in the olfactory stimuli control system according to the current invention.

Now referring to FIG. 12, a fourth preferred embodiment of the releasing unit according to the current invention is illustrated in a perspective view. In general, the fourth preferred embodiment thermally initiates the release of aromatic agent. As a sheet of thermally sensitive aroma-releasing material 1100 is rolled in a direction as indicated by an arrow towards a retracting roller 1203, an unused portion of the sheet is heated by a thermal head 1201 over a platen roller 1202.

Figure 13A:
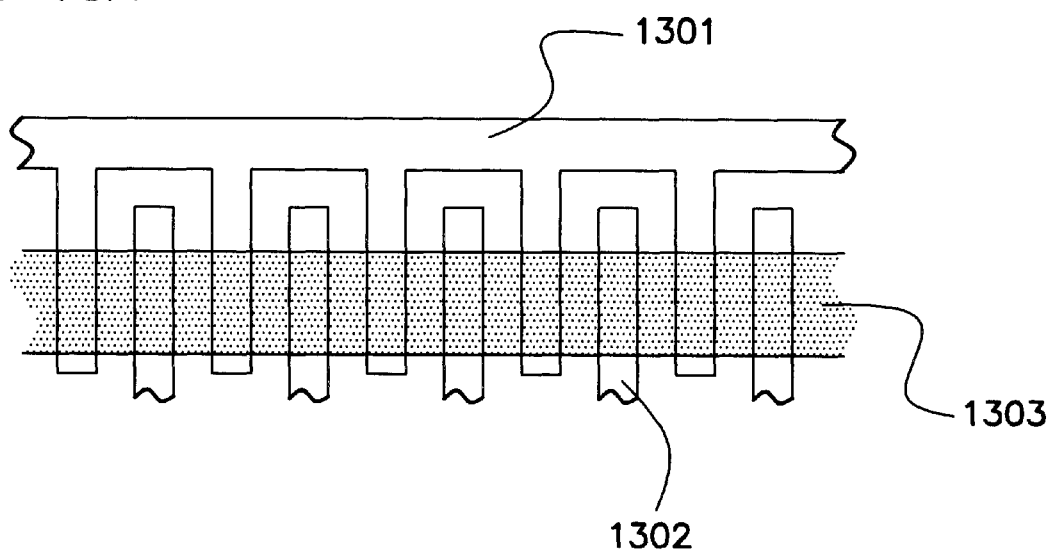
FIGS. 13A and 13B are respectively a top view and a cross sectional view of the fourth preferred embodiment of the releasing unit used in the olfactory stimuli control system according to the current invention.
Figure 13B:
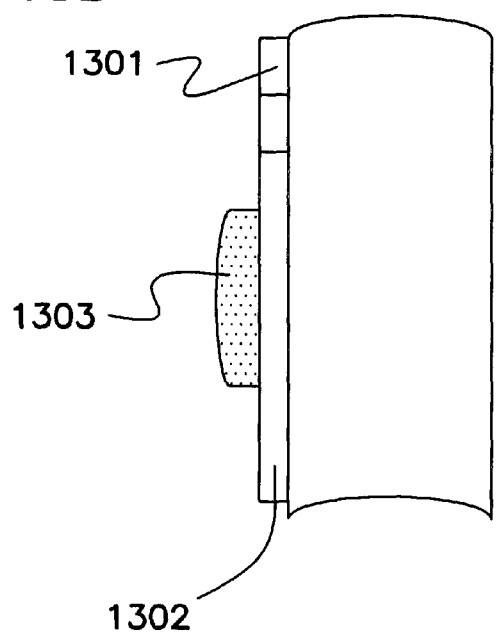

FIGS. 13A and 13B respectively illustrate a top view and a side view of one implementation of the above described thermal head. This implementation of the thermal head includes a common electrode 1301, a separate electrodes 1302 and an optimally placed resistor 1303 which generates heat. According to the implementation, the heat generating resistor is located above the electrodes 1301 and 1302 and transfers heat onto the a heat-sensitive medium.

Figure 14A:
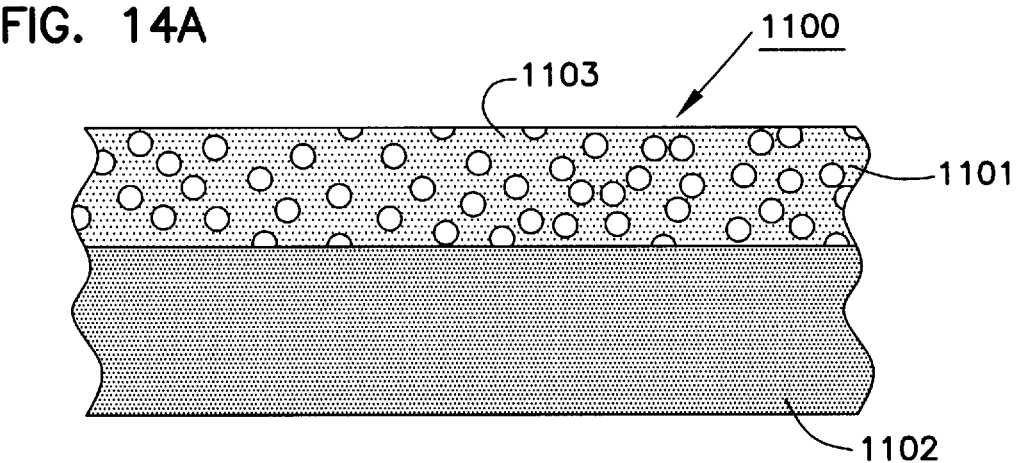
FIGS. 14A and 14B are respectively a cross sectional view and a top view of another aroma storage unit used in conjunction with the fourth preferred embodiment of the releasing unit in the olfactory stimuli control system according to the current invention.
Figure 14B:
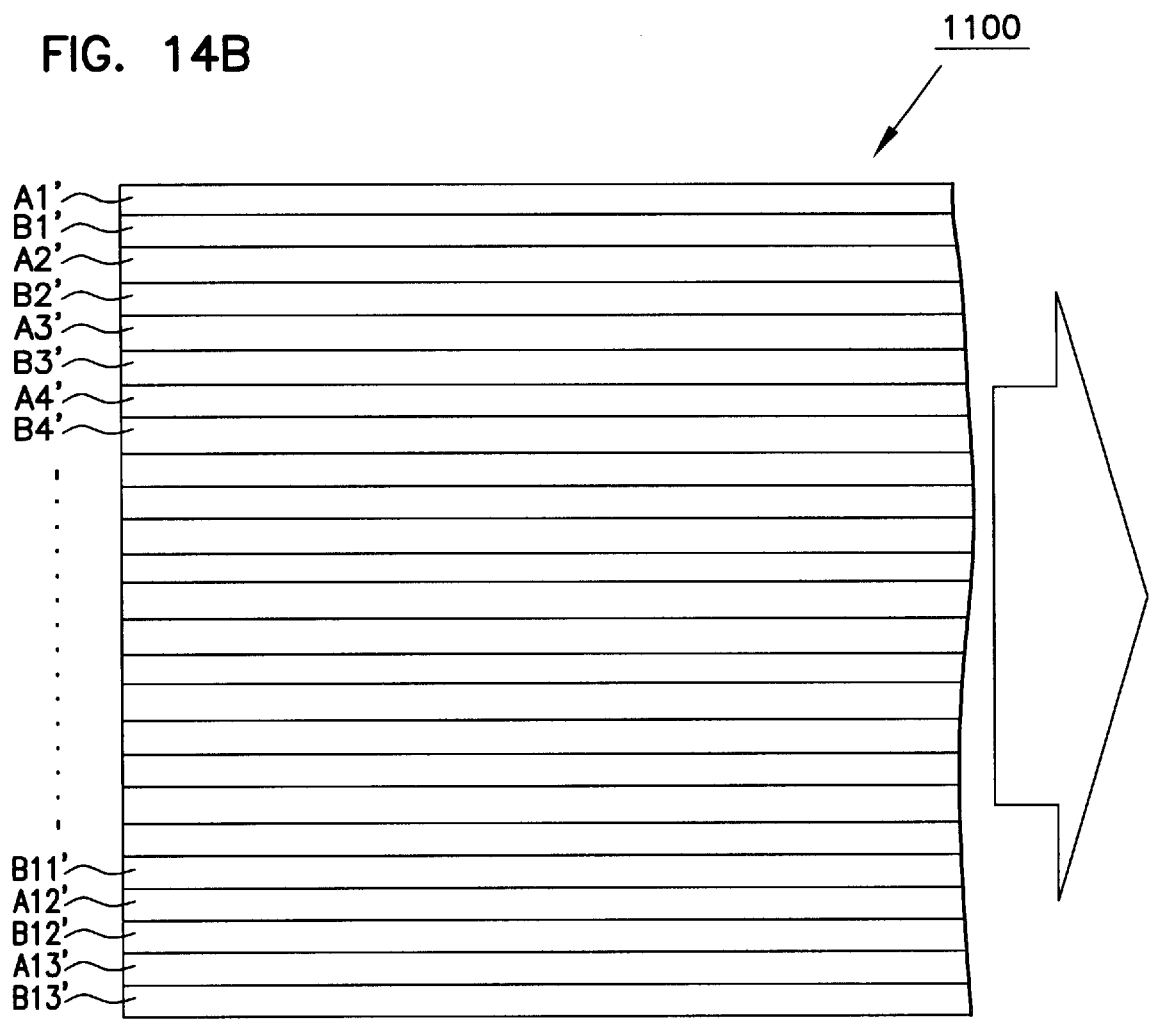

FIGS. 14A and 14B respectively illustrate a cross sectional view and a top view of the heat-sensitive aroma roll 1100. One exemplary construction of the heat-sensitive roll 1100 contains an aroma-causing agent and or an aroma-removing agent which are represented by particles 1101. The particles 1101 are generally imbedded in a binder material 1103, and the binder material 1103 containing the particles 1101 is placed over a base medium 1102 such as a sheet of paper, cloth or plastic. As shown in FIG. 14B, a collection of the above described strips each containing a distinct aromatic agent forms the roll 1100. According to one preferred embodiment, aroma-causing agent containing strips A1' through A13' and aroma-removing agent containing strips B1' through B13' are alternately juxtaposed in the direction of moving the roll 1100. When a particular strip is heated by a corresponding individual electrode 1302 as shown in FIG. 13A, an aroma from the particles 1101 is released into the air.

Figure 15:
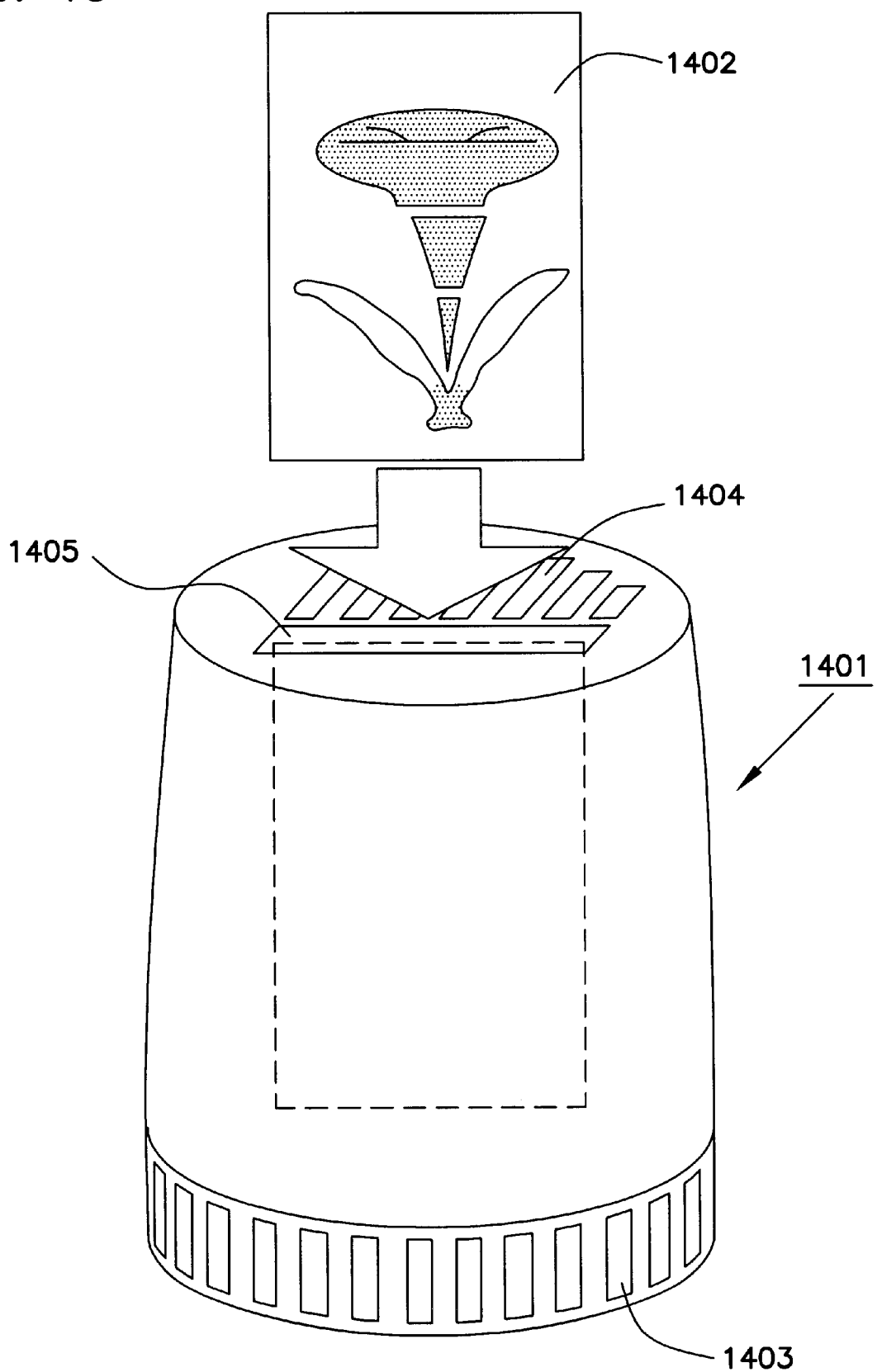
FIG. 15 is a perspective view of a second preferred embodiment of the olfactory stimuli control system according to the current invention.

Now referring to FIG. 15, a second preferred embodiment of the olfactory stimuli control system according to the current invention is illustrated in a perspective view. Although the second embodiment is illustrated as a portable desk-top unit for generating aroma in a confide space, alternative embodiments include one or more of the following unique features. In general, the second preferred embodiment of the olfactory stimuli system includes a memory card 1402 and a portable unit 1401. The portable unit 1401 has an opening 1405 for accepting the memory card 1402 for reading information stored on a magnetic surface and uses the information in generating an aroma. The memory card 1402 also has a second decorated surface for indicating a type of a scent in a picture. The portable unit 1402 inputs fresh air through an input vent 1403 and outputs the scented air through an output vent 1404. In addition to the information input by the memory card 1402, the portable unit 1401 measures a certain predetermined characteristic of the environment and generates an aroma based upon the memory card information and the measured characteristic.

Referring to FIG. 16A, one example of information contained in the above described memory card 1402 is illustrated in a table format. Depending upon a combination of temperature and humidity of the environment, a scent is selected. The information also specifies an amount of time for releasing the selected scent and an associated releasing unit from which the selected scent is released. Lastly, each scent is numbered by a unique number. Although this example shows that the humidity dictates over the temperature, the combination is not limited to the above priority or the two environmental factors. Furthermore, the above exemplary information is also stored in an internal permanent storage such as a read only memory (ROM) and is used as default information in the absence of any inputted information to override the default information.

Figure 16B:
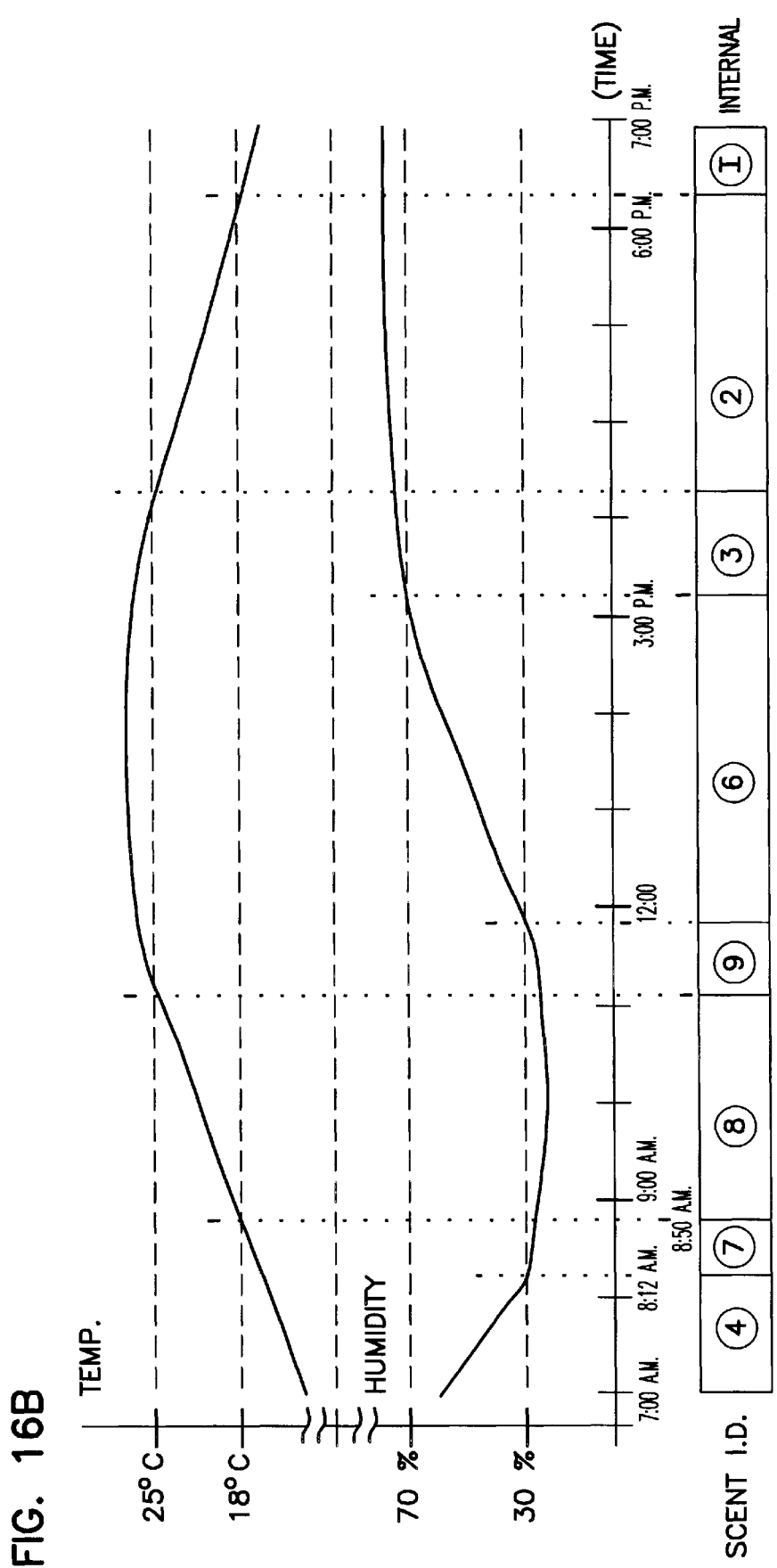
FIG. 16B is a graph illustrating continuous selection of a scent over a specified time period based upon temperature and humidity as specified in the above exemplary table in FIG. 16A.

FIG. 16B is a graph illustrating continuous selection of a scent over a specified time period based upon temperature and humidity as specified in the above exemplary table in FIG. 16A. The olfactory stimuli control system according to the current invention periodically monitors scent selection criteria such as temperature and humidity and selects an aroma based upon the actually measured temperature and humidity values for continuously releasing the same aroma until a new aroma is selected. For example, between 7:00 AM and 8:12 AM, on a particular day, assuming that humidity is between 30% and 70% while temperature is below 18° C., a mango scent is selected according to the above information table. However, after 8:12 AM, since humidity changes below 30% while temperature remains below 18° C., a papaya scent is now selected. At 8:50 AM, since temperature changes above 18° C. while humidity stays below 30%, a beech tree scent is selected. By the same manner, temperature and humidity are continuously monitored and a scent is continuously selected based upon the combination of the measured values until 7:00 PM according to this example.

FIG. 16C is another exemplary table of information on a sequential selection of scents used in the olfactory stimuli control system according to the current invention. For example, the sequential selection information is stored in a card memory in a predetermined manner. In general, upon reading the card memory, the olfactory stimuli control system according to the current invention overrides an ongoing operation and sequentially releases a series of the scents specified in the card memory. According to this exemplary information, in a first event, negative ions are released for 180 second, and in a second event, a mugwort scent is released from a A6 releasing unit for 20 seconds at a time for 120 seconds in total with a 50 second interval. A sequence of other scent releases and scent removals is performed as specified in the card memory until the tenth event is completed.

Figure 17:
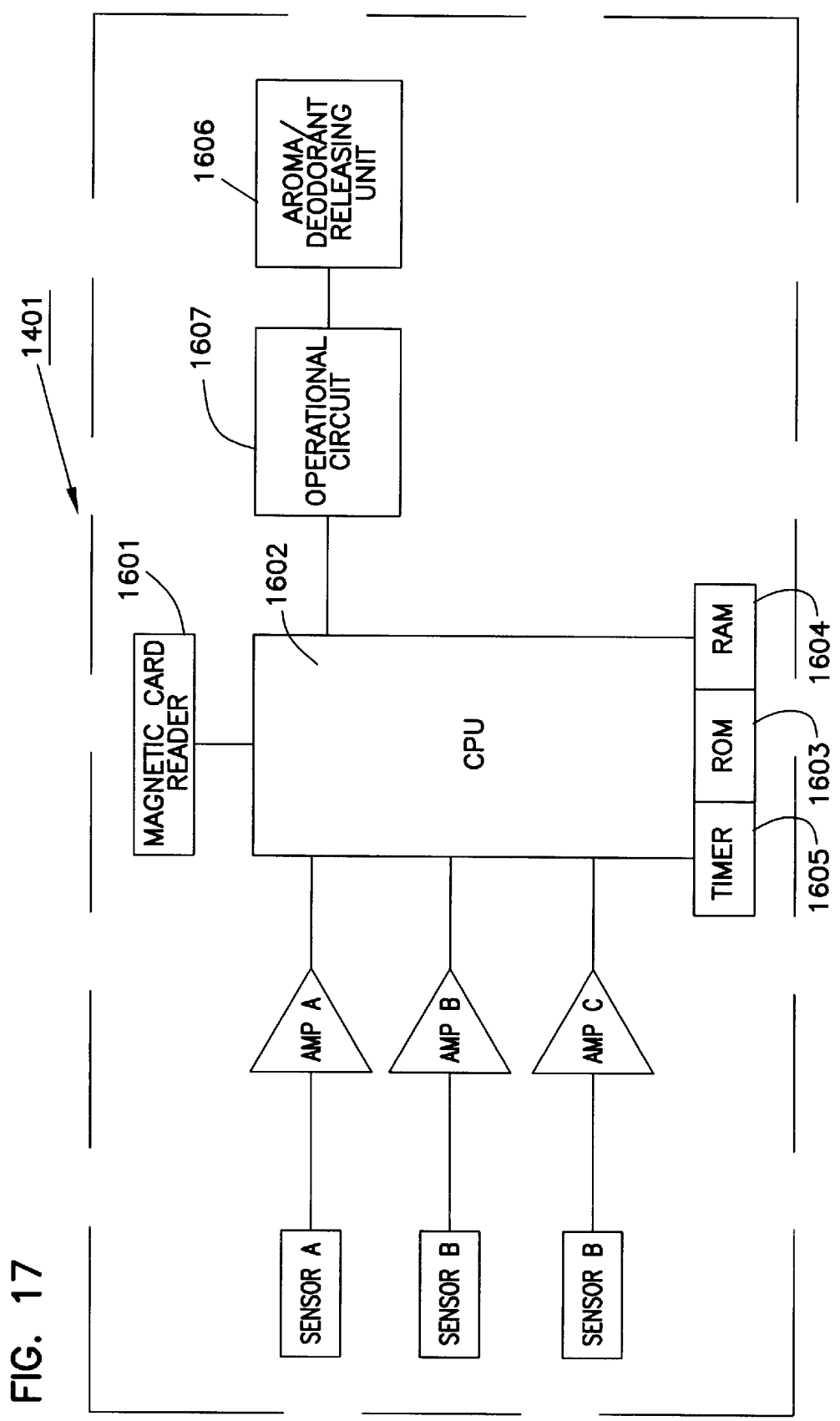
FIG. 17 is a circuit diagram of the second preferred embodiment of the olfactory stimuli control system according to the current invention.

Referring to FIG. 17, the above described second preferred embodiment of the olfactory stimuli control system according to the current invention is illustrated in a circuit diagram. The second preferred embodiment 1401 includes a card reader 1601, a set of predetermined sensors and amplifiers, a central processing unit (CPU) 1602, a timer 1605, a read-only memory unit (ROM) 1603, a random-access memory unit 1604, an operational circuit 1607 and an aroma releasing unit 1606. In general, the sensors A, B and C respectively measure a predetermined characteristic and generate corresponding environmental signals. The sensor A includes a thermistor and measures the environmental temperature. The sensor B includes a pair of thermistors and measures humidity. The sensor C includes an odor detector such as a metal oxide semiconductor for detecting cigarette odor. Amplifiers A, B and C respectively amplify and digitally convert the environmental signals.

Still referring to FIG. 17, the CPU 1602 receives the above described memory card information from the card reader 1601, as well as the environmental signals from the sensors A, B and C. The CPU 1602 also reads control programs as well as some default information from the ROM 1603. The CPU 1602 then tentatively stores the above information, program and signals in a RAM 1604. If the memory card information is available, the CPU 1602 determines which aroma is to be generated based upon the environmental signal in reference to the memory card information. On the other hand, if the memory card information is not available, the CPU 1602 determines which aroma is to be generated based upon the environmental signal and the default information from the ROM 1603. After selecting an aroma, the CPU 1602 accordingly controls the operational circuit 1607 for releasing a selected aroma or a combination of the selected aromas via the aroma releasing unit 1606. The CPU 1602 also stores information on the currently released aroma so that prior to releasing a next aroma, the previously released aroma is substantially removed, neutralized or weakened by releasing a corresponding aroma-removing agent based upon the stored information. The timer 1605 is used for controlling the duration of the release as well as tracking an amount of time between releases of any aroma. Lastly, although the above described second preferred embodiment is illustrated as an independent unit with a card reader input, the second preferred embodiment is also interfaced with other input devices or a network for inputting aroma release information.

Figure 18:
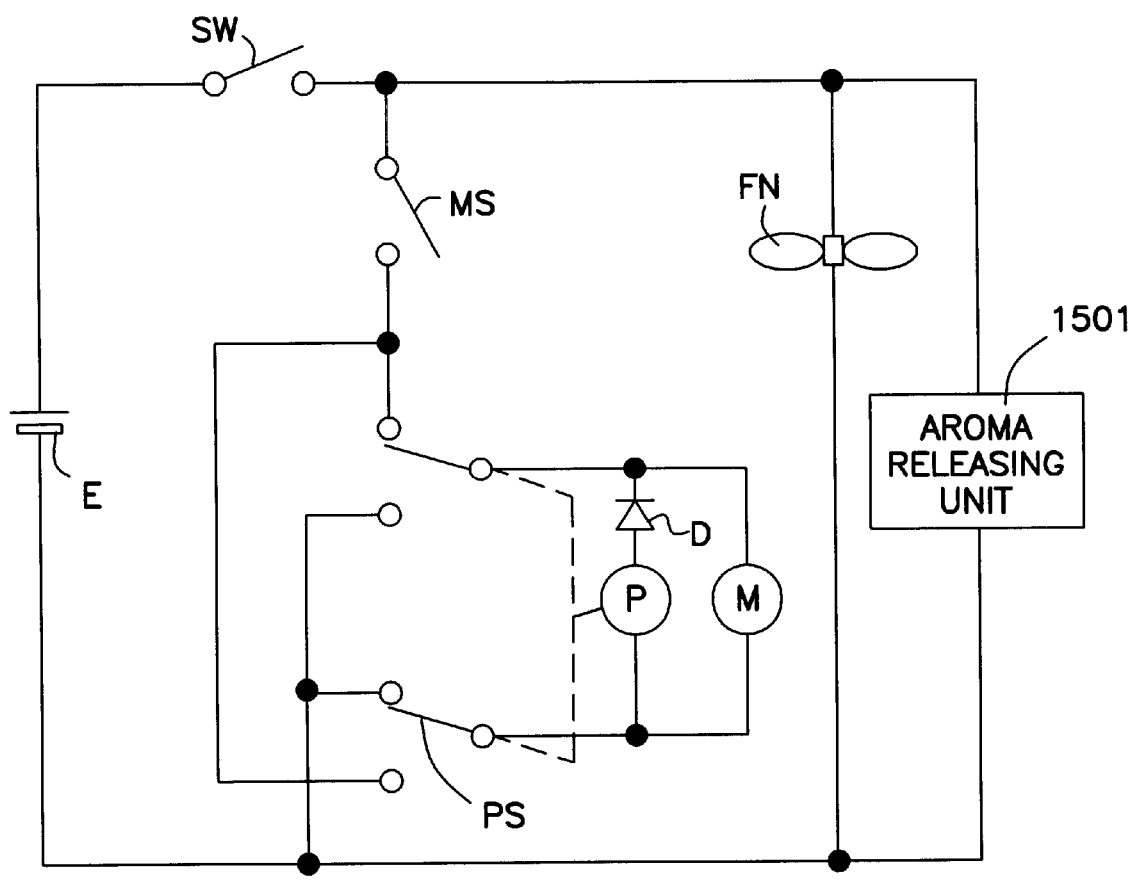
FIG. 18 is a circuit diagram of an input card reader in the second preferred embodiment of the olfactory stimuli control system according to the current invention.

Referring to FIG. 18, the above described card reader 1601 is further described in a circuit diagram along with an aroma releasing unit 1501 which releases an aroma-causing agent and or an aroma-removing agent and a fan FN is located in the vicinity of the aroma releasing unit 1501. When a memory card is partially inserted into the olfactory stimuli unit, the card edge closes a micro switch MS which activates a memory card transfer motor M for automatically transferring the card to the fully inserted position. The memory card transfer motor M is powered by a power source E. During the transfer, the information is read from the memory card. At the fully inserted position, the leading edge of the memory card turns a plunger switch PS to an alternate position for causing the transfer motor M to rotate in an opposite direction. Consequently, the memory card is ejected, and the plunger switch PS is reverted to an original position while the micro switch MS is turned off.

Figure 19:
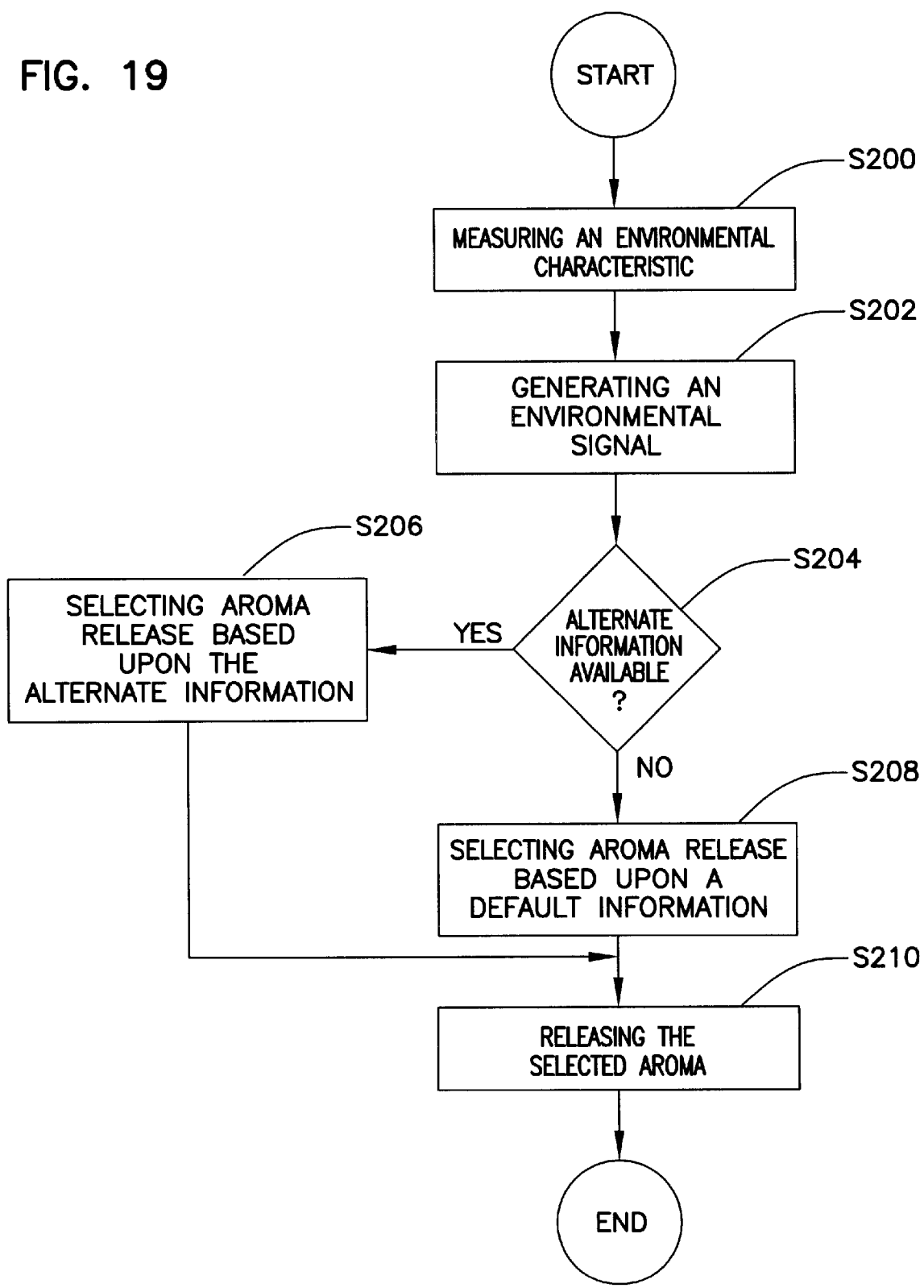
FIG. 19 is a flow chart describing the steps involved in a second preferred process according to the current invention.

Referring to FIG. 19, some critical steps of the second preferred process of generating an olfactory stimulus according to the current invention are illustrated in a flow chart. In general, the second preferred process includes a step of measuring at least one predetermined environmental characteristic in a step S200. The predetermined characteristic includes temperature, humidity and a presence of a certain odor. Based upon the measuring step S200, a corresponding environmental signal is generated in a step S202. The environmental signal is used to select an aroma from either a default source of data or an alternate source of information. In a step S204, if the alternative source of information is available after inputted for example by a memory card, a certain scent is selected from the inputted information based upon the environmental signal in a step S206. On the other hand, if the alternative source of information has not been inputted, based upon the environmental signal, a certain scent is selected from a default set of data which has been stored for example in a ROM in a step S208. Finally, the selected scent is released in a step S210. The above steps may be automatically repeated with a predetermined interval in the absence of a user selection of an aroma. Alternative processes of generating an olfactory stimulus according to the current invention include a combination of the above described first and second preferred processes. In other words, the combined alternative process include additional steps of storing information on the aroma which has been selected based upon an environmental characteristic as well as substantially eliminating the released aroma by neutralizing, weakening or overpowering with a corresponding aroma-removing agent. The combined alternative process optionally further includes a step of releasing a new aroma after the first aroma has been substantially eliminated. Another alternative process includes a step of inputting the alternative source of information. As shown in an exemplary table of FIG. 16, the alternative source of information may include a different order of parameters, a different set of ranges for each parameter as well as a different set of aromas to be released.

Figure 20:
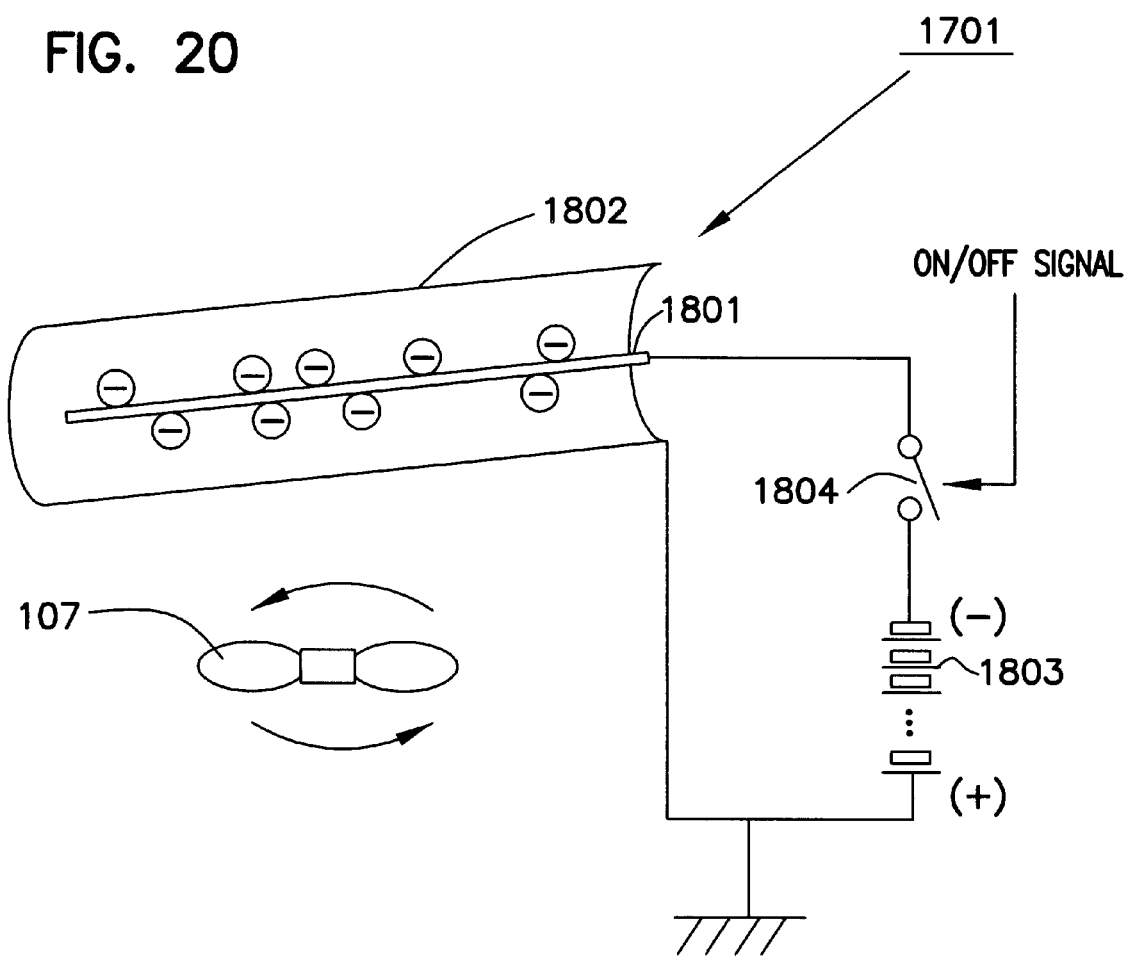
FIG. 20 is a circuit diagram of a negative ion generation unit optionally used in the olfactory stimuli control system according to the current invention.

Now referring to FIG. 20, to effectively remove a residual aroma from a previous release, one preferred embodiment of the olfactory stimuli control system includes a negative ion generation unit 1701, which may be placed near a fan 107. The circuit diagram illustrates a metal wire 1801, a metal plate 1802, a power source 1803 and a switch 1804. In general, it has been known that negative ions are generally perceived as a pleasant odor, and the negative ions can be also combined with an aroma-removing agent.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of controlling olfactory stimuli in a limited space, comprising the steps of:
   a') providing a plurality of aromas;
   a") placing a network of olfactory releasing stations at predetermined locations;
   a) selecting a first releasing location among the predetermined locations based upon an input signal which is at least indicative of a location and one of the plurality of the aromas from which an aroma-causing agent is selected;
   b) releasing the aroma-causing agent based upon the input signal from the first releasing location;
   c) selecting at least a second releasing location; and
   d) releasing the aroma-causing agent based upon the input signal from the second releasing location to simulate a movement of the aroma in space.

2. The method of controlling the olfactory stimuli according to claim 1 wherein said input signal includes information on a directionality and a delay time and further comprises additional steps of c) selecting a second releasing location based upon the input signal and d) releasing the aroma-causing agent from the second releasing location after a certain time specified in the input signal.

3. The method of controlling the olfactory stimuli according to claim 1 further comprising an additional step of e) of releasing a first aroma-removing agent near the first releasing location.

4. The method of controlling olfactory stimuli according to claim 3 wherein said input signal also indicates strength of the aroma-causing agent.

5. The method of controlling olfactory stimuli according to claim 1 wherein the aroma-causing agent is stored in a liquid form.

6. The method of controlling olfactory stimuli according to claim 1 wherein the aroma-causing agent is stored in a solid form.

7. The method of controlling olfactory stimuli according to claim 1 wherein the aroma-causing agent is a mixture of a plurality of aroma-causing elements.

8. The method of controlling olfactory stimuli according to claim 1 wherein said steps a) and b) are performed in the environment where audio-visual stimuli are provided to complement the olfactory stimuli.

9. The method of controlling olfactory stimuli according to claim 2 wherein the first releasing location and the second releasing location are in a network environment.

10. A system for controlling olfactory stimuli, comprising:
    an input signal unit for inputting an input signal indicative of a first location, a second location and an aroma-causing agent;
    a plurality of aromas and non-aroma stimuli;
    a control unit connected to said input signal unit for generating a first location signal and a second location signal based upon the input signal;
    a network of aroma releasing units each connected to said control unit, each of said aroma releasing units having access to said aromas further comprising:
    a storage unit for storing an aroma-causing agent;
    a first releasing unit located near the first location and connected to said storage unit and said control unit for releasing said aroma-causing agent in environment based upon the first location signal wherein the input signal indicative of a first location signal for activating a first one of said aroma releasing units that is located near the first location, the input signal also indicating which one of said aromas that contains said aroma-causing agent; and
    a second releasing unit located near the second location and connected to said storage unit and said control unit for releasing said aroma-causing agent in environment based upon the second location signal wherein the input signal indicative of a second location signal for activating a first one of said aroma releasing units that is located near the second location, the input signal also indicating which one of said aromas that contains said aroma-causing agent, wherein the system stimulates a movement of the aroma in space.

11. The system for controlling the olfactory stimuli according to claim 10 further comprising a second releasing unit, said input signal unit further inputs information on a directionality and a delay time via the input signal, said control unit generating a second location signal for a second location based upon the input signal, said second releasing unit located substantially near the second location for releasing the aroma-causing agent after a certain time specified in the input signal.

12. The system for controlling the olfactory stimuli according to claim 10 wherein said first releasing unit releases a first aroma-removing agent near the first location for removing the aroma-causing agent.

13. The system for controlling olfactory stimuli according to claim 10 wherein the input signal also indicates strength of the aroma-causing agent.

14. The system for controlling olfactory stimuli according to claim 10 wherein the aroma-causing agent is stored in a liquid form.

15. The system for controlling olfactory stimuli according to claim 10 wherein the aroma-causing agent is stored in a solid form.

16. The system for controlling olfactory stimuli according to claim 10 wherein the aroma-causing agent is a mixture of a plurality of aroma-causing elements.

17. The system for controlling olfactory stimuli according to claim 10 further comprising an audio-visual unit for providing audio-visual stimuli in the environment to complement the olfactory stimuli.

18. The system for controlling olfactory stimuli according to claim 12 wherein the first location and the second location are in a network environment.

* * * * *